US009708662B2

(12) United States Patent
Sextius et al.

(10) Patent No.: US 9,708,662 B2
(45) Date of Patent: Jul. 18, 2017

(54) MOLECULAR SIGNATURE REPRESENTATIVE OF DYSFUNCTIONS IN EPIDERMAL HOMEOSTASIS

(75) Inventors: Peggy Sextius, Fontenay sous Bois (FR); Bruno Bernard, Courbevoie (FR); Françoise Bernerd, Paris (FR); Claire Marionnet, Ville-D'Avray (FR)

(73) Assignee: L'Oreal, Paris (FR)

( * ) Notice: Subject to any disclaimer, the term of this patent is extended or adjusted under 35 U.S.C. 154(b) by 71 days.

(21) Appl. No.: 12/458,772

(22) Filed: Jul. 22, 2009

(65) Prior Publication Data

US 2010/0055694 A1  Mar. 4, 2010

Related U.S. Application Data

(60) Provisional application No. 61/095,360, filed on Sep. 9, 2008.

(30) Foreign Application Priority Data

Jul. 22, 2008  (FR) ..................... 08 04169

(51) Int. Cl.
  *C12Q 1/68*  (2006.01)
  *C07H 21/02*  (2006.01)
(52) U.S. Cl.
  CPC ..... *C12Q 1/6883* (2013.01); *C12Q 2600/136* (2013.01); *C12Q 2600/158* (2013.01)
(58) Field of Classification Search
  CPC ............ C12Q 1/6883; C12Q 2600/136; C12Q 2600/158
  See application file for complete search history.

(56) References Cited

FOREIGN PATENT DOCUMENTS

WO  WO2005/100603  10/2005

OTHER PUBLICATIONS

Cole, J. et al., Wound Rep. Reg., vol. 9, pp. 360-370 (2001).*
Enk, C.D. et al., Photoderm., Photoimm., Photomed., vol. 20, pp. 129-137 (2004).*
Lippens, S. et al., Cell Death Diff., vol. 12, pp. 1497-1508 (2005).*
Loden, M. et al., Acta Derm. Venereol., vol. 80, pp. 412-415 (2000).*
Wetzel, J. et al., Contact Dermatitis, vol. 35, pp. 163-168 (1996).*
Family Doctor, "How UV radiation affects your skin" downloaded from familydoctor.co.uk/info/skin-how-uv-radiation-affects-your-skin on Jun. 15, 2012.*
Bustin, S.A. et al., J. Mol. Endocrinol., vol. 25, pp. 169-193 (2000).*
Paladini, R.D. et al., J. Cell Biol., vol. 132, pp. 381-397 (1996).*
Sextius, P. et al., Exp. Dermatology, vol. 19, pp. 259-268 (2010).*
Elias, P.M., J. Invest. Dermatol., vol. 125, pp. 183-200 (2005).*
Ding, Y. et al., nJ. Biomol. Techniques, vol. 18, pp. 321-330 (2007).*
de Jonge, H.J.M. et al., PLoS One, vol. 2, e898, pp. 1-5 (2007).*
Barel, A. O. et al. "Study of the Stratum Corneum Barrier Function by Transepidermal Water Loss Measurements: Comparison Between Two Commercial Instrument: Evaporimeter and Tewameter" *Skin Pharmacol* 1995 vol. 8 pp. 186-195.
Denda M. "New Strategies to Improve Skin Barrier Homeostasis" *Adv. Drug Deliv Rev*; 54 Suppl 1 Jan. 11, 2002 pp. S123-S130.
Ghadially R. et al. "The Aged Epidermal Permeability Barrier, Structural, Functional, and lipid biochemical Abnormalities in Humans and Senescent Murine Model" *J Clin Invest* 1995 vol. 95 No. 5 pp. 2281-2290.
Grubauer, G et al. "Lipid Content and Lipid Type as Determinants of the Epidermal Permeability Barrier" *Journal of Lipid Research* 1989 vol. 30 pp. 89-96.
Grubauer, G. et al. "Relationship of Epidermal Lipogenesis to Cutaneous Barrier Function" *Journal of Lipid Research* 1987 vol. 28 pp. 746-752.
Kuss, O et al. "Proper Statistical Analysis of Transepidermal Water Loss (TEWL) Measurements in Bioengineering Studies" *Contact Dermatitis* 1998 vol. 39 pp. 64-67.
Leveque, J. L. "Quantitative Assessment of Skin Aging" *Clinics in Geriatric Medicine* 2001 vol. 17 No. 4 pp. 673-689.
Lock-Andersen, J. et al. "Epidermal Thickness, Skin Pigmentation and Constitutive Photosensitivity" *Photodermatol Photoimmunol Photomed* 1997 vol. 13 pp. 153-158.
Marionnet, C. et al. "Modulation of Gene Expression Induced in Human Epidermis by Environmental Stress in Vivo" *J Invest Dermatol* vol. 121 pp. 1447-1458, 2003.
Menon, G. K. et al. "De Novo Sterologenesis in the Skin. II. Regulation by Cutaneous Barrier Requirements" *J Lipid Res* 1985 vol. 26 pp. 418-427.
Piaserico, S. et al. "Allergic Contact Sensitivity in Elderly Patients" *Aging Clin Exp.* vol. 16 No. 3 pp. 221-225, 2004.
Piepkorn, M. et al. "Amphiregulin-Dependent Proliferation of Cultured Human Keratinocytes: Autocrine Growth, the Effects of Exogenous Recombinant Cytokine, and Apparent Requirement for Heparin-Like Glycosaminoglycans" *J Cell Physiol* 1994 vol. 159 pp. 114-120.
Pinnagoda, J. et al. "Guidelines for Transepidermal Water Loss (TEWL) Measurement" *Contact Dermatitis* 1990 vol. 22 pp. 164-178.
Proksch, E. et al. "Barrier Function Regulates Epidermal DNA Synthesis" *J Clin Invest* vol. 87 pp. 1668-1673, 1991.

(Continued)

*Primary Examiner* — Teresa Strzelecka
(74) *Attorney, Agent, or Firm* — Buchanan Ingersoll & Rooney PC

(57) ABSTRACT

The present invention concerns a method for evaluating the epidermal homeostasis of the skin of a subject, comprising differential analysis of the expression of a gene, preferably of two genes, selected from the group of genes consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN in response to a physical or chemical challenge of the stratum corneum. It also concerns various methods for diagnosing the state of the epidermis of an individual and methods for detecting and screening products or procedures which can improve epidermal homeostasis. The invention also pertains to kits and arrays which can be used in these various methods and processes.

14 Claims, 7 Drawing Sheets

(56) References Cited

OTHER PUBLICATIONS

Tanaka, M. et al. "Normal Recovery of the Stratum Corneum Barrier Function Following Damage Induced by Tape Stripping in Patients with Atopic Dermatitis" *British Journal of Dermatology* 1997 vol. 136 pp. 966-967.

Treffel, P. et al. "Hydration, Transepidermal Water Loss, PH and Skin Surface Parametr: Correlations and Variations Between Dominant and non-Dominant Forearms" *British Journal of Dermatology* 1994 vol. 130 pp. 325-328.

Van, S. V. et al. "TEWL Measurement Standardization: Kinetic and Topographic Aspects" *Acta Derm. Venereol* 1994 vol. 74 pp. 168-170.

Wood, L. C. et al. "Cutaneous Barrier Perturbation Stimulates Cytokine Production in the Epidermis of Mice" *J Clin Invest* 1992 vol. 90 pp. 482-487.

Zhai, H. et al. "Human Barrier Recovery After Acute Acetone Perturbation: an Irritant Dermatitis Model" *Clinical and Experimental Dermatology* 1998 vol. 23 pp. 11-13.

Ye, J et al. "Alterations in Cytokine Regulation in Aged Epidermis: Implications for Permeability Barrier Homeostasis and Inflammation" *Experimental Dermatology* 2002 vol. 11 No. 3 pp. 209-216 XP002522056.

Curto, E et al. "Biomakers of Human Skin Cells Identified Using DermArray DNA Arrays and New Bioinformatics Methods" *Biochemical and Biophysical Research Communications* 2002 vol. 291 No. 4 pp. 1052-1064 XP002265763.

Eung-Ho, C. et al. "Stratum Corneum Acidification is Impaired in Moderately Aged Human and Murine Skin" *The Journal of Investigative Dermatology* 2007 vol. 127 No. 12 pp. 2847-2856 XP002522058.

Barland, C. et al. "Imiquimod-Induced Interleukin-1α Stimulation Improves Barrier Homeostasis in Aged Murine Epidermis" *The Jurnal of Investigative Dermatology* 2004 vol. 122 No. 2 pp. 330-336 XP002522059.

Elias P.M. et al. "The Aged Epidermal Permeability Barrier: Basis for Functional Abnormalities . . . " *Clinics in Geriatric Medicine* 2002 vol. 18 No. 1 pp. 103-120 XP009114232.

International European Search Report PCT/EP09/166054 dated Sep. 16, 2009.

International French Search Report PCT/FRO8/04169 dated Apr. 3, 2009.

* cited by examiner

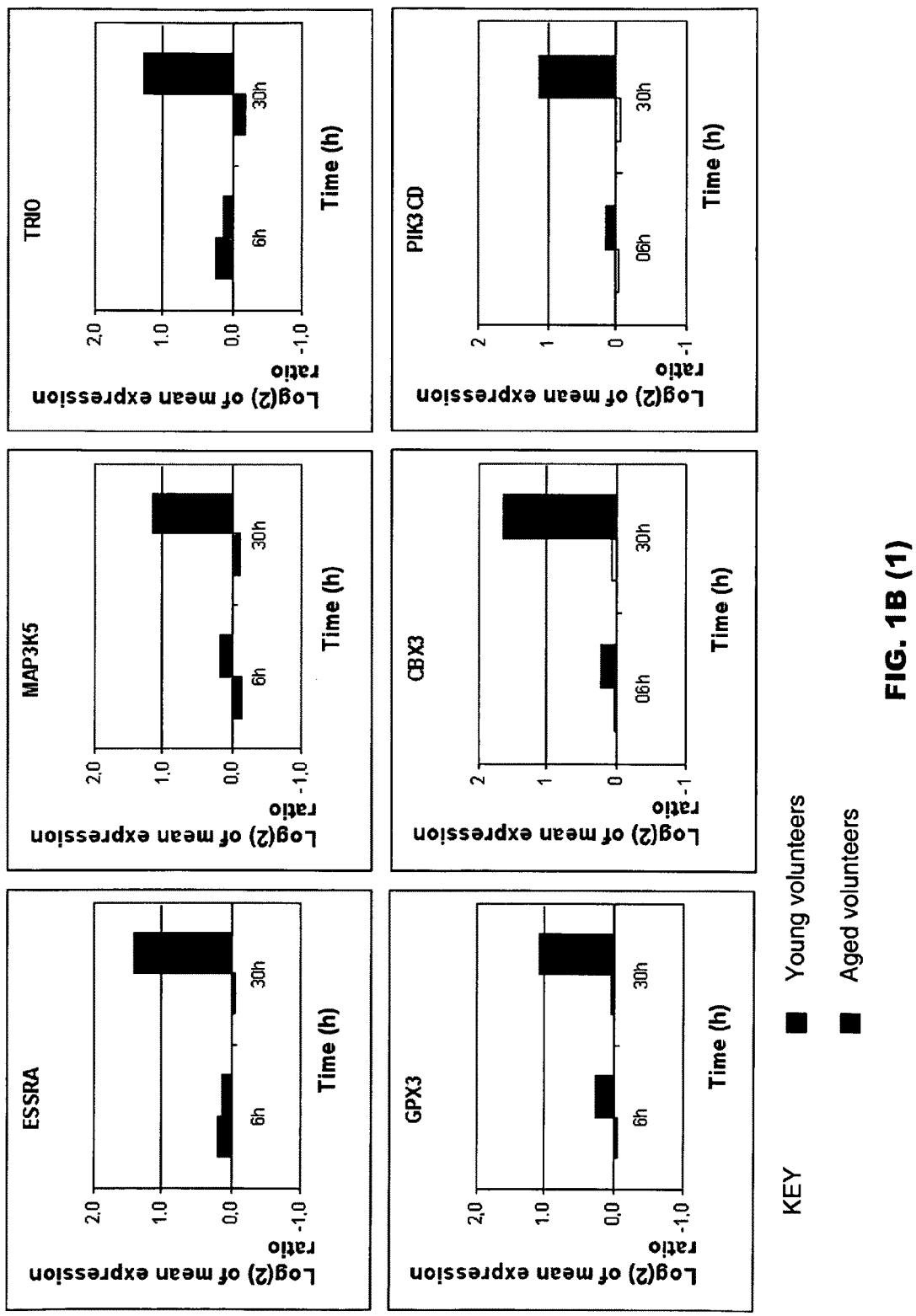
FIG. 1B (1)

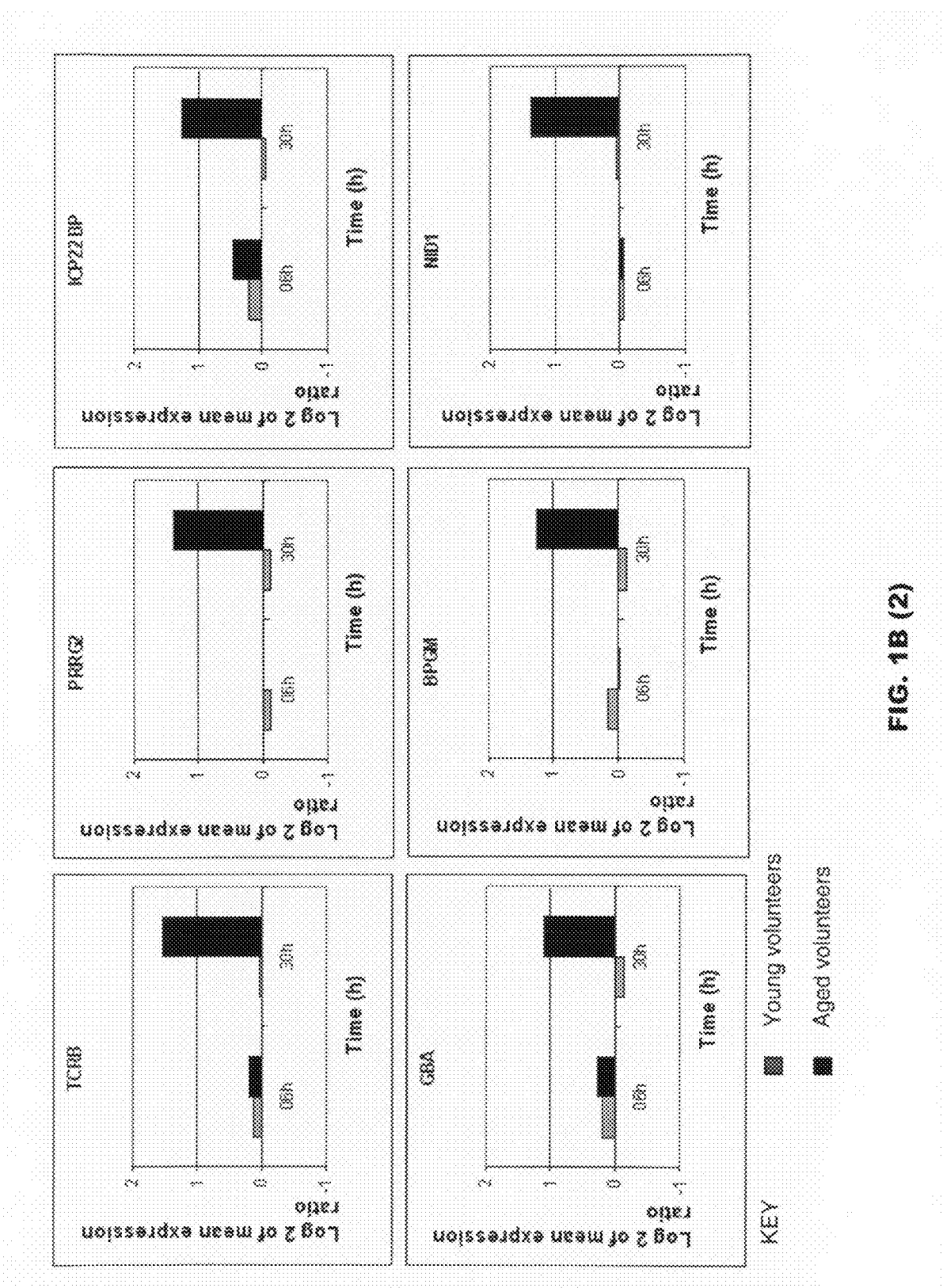
FIG. 1B (2)

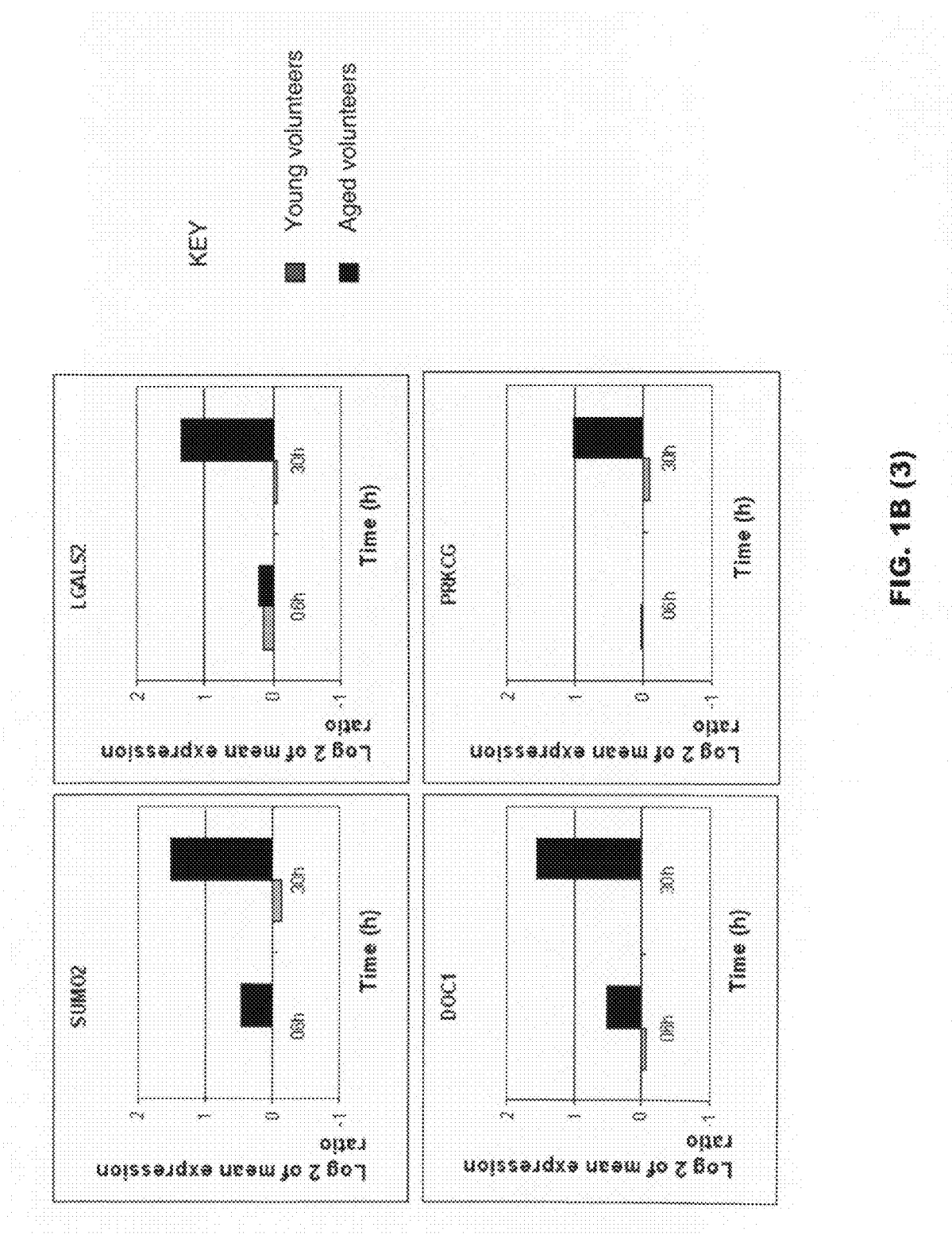
FIG. 1B (3)

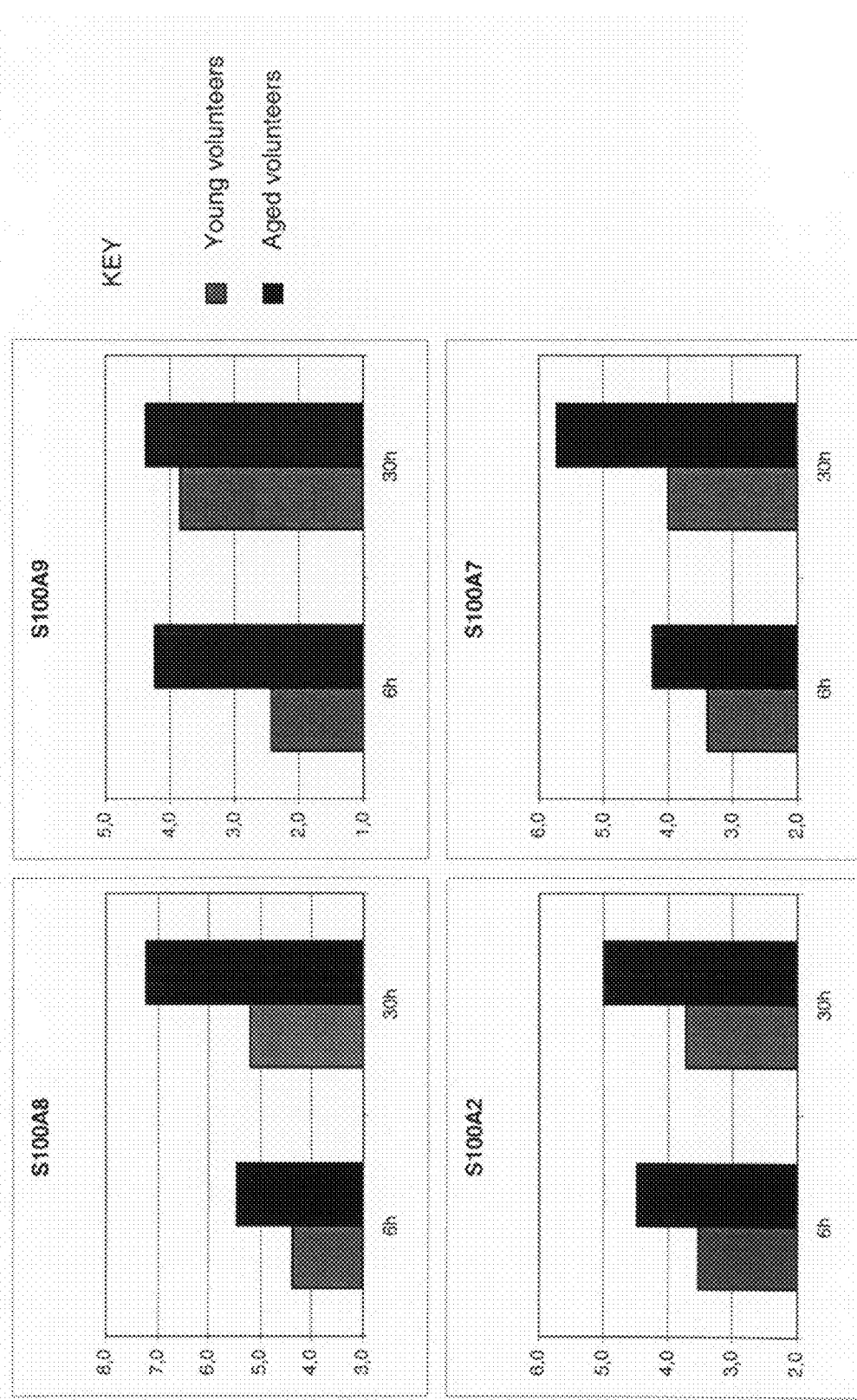
FIG. 2 (1)

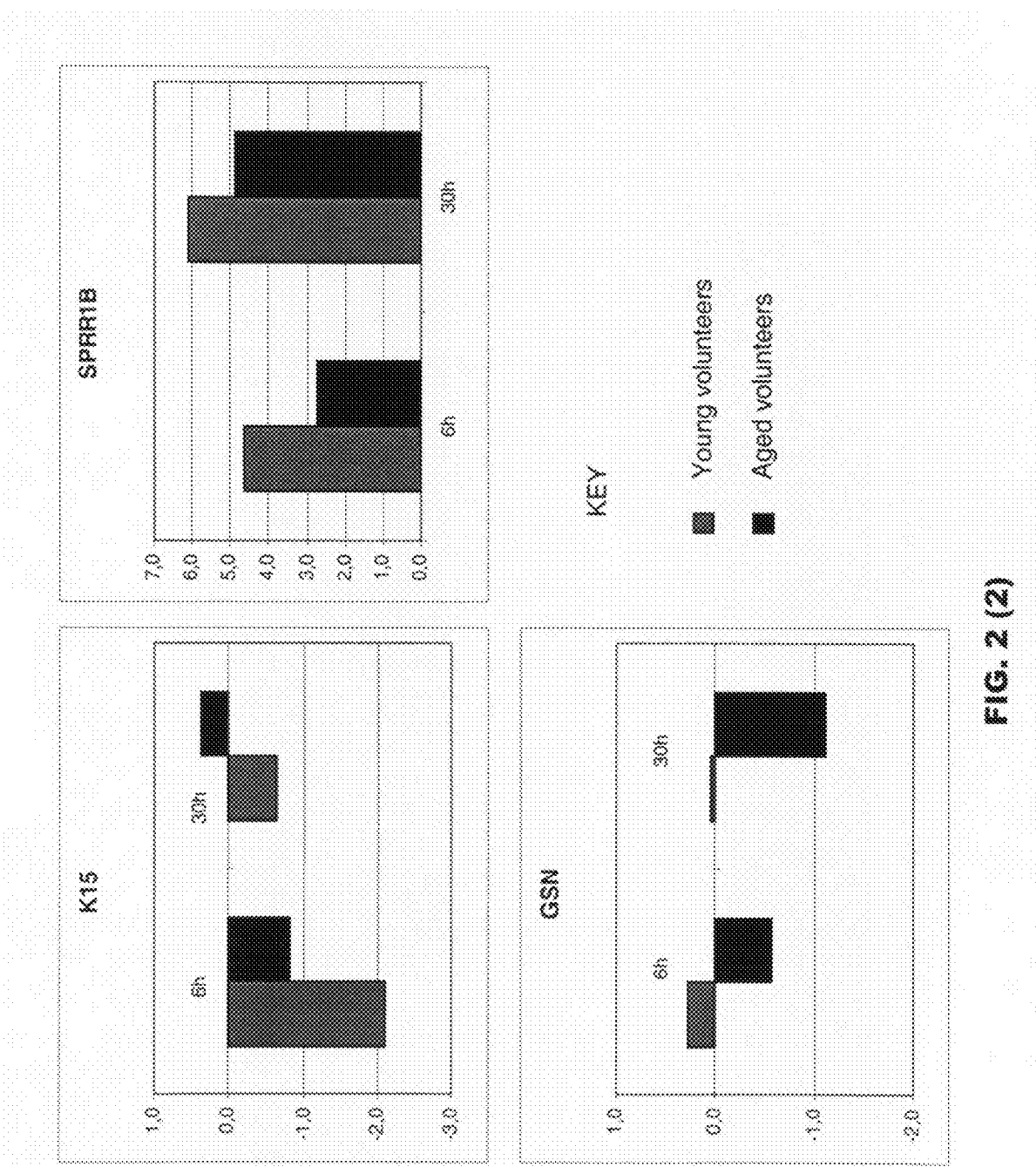
FIG. 2 (2)

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial
<220> FEATURE:
<223> OTHER INFORMATION: Amorce/primer

<400> SEQUENCE: 1
cctatctcag ggagggaagg                                                 20

<210> SEQ ID NO 2
<211> LENGTH: 20
<212> TYPE: DNA
<213> ORGANISM: Artificial
<220> FEATURE:
<223> OTHER INFORMATION: Amorce/primer

<400> SEQUENCE: 2
tctccaagtc ccactctgct                                                 20

<210> SEQ ID NO 3
<211> LENGTH: 20
<212> TYPE: DNA
<213> ORGANISM: Artificial
<220> FEATURE:
```

```
<223> OTHER INFORMATION: Amorce/primer

<400> SEQUENCE: 3
ttggcagttt aggacctgct                                              20

<210> SEQ ID NO 4
<211> LENGTH: 20
<212> TYPE: DNA
<213> ORGANISM: Artificial
<220> FEATURE:
<223> OTHER INFORMATION: Amorce/primer

<400> SEQUENCE: 4
gttcttcctg gcttttgctg                                              20

<210> SEQ ID NO 5
<211> LENGTH: 27
<212> TYPE: DNA
<213> ORGANISM: Artificial
<220> FEATURE:
<223> OTHER INFORMATION: Amorce/primer

<400> SEQUENCE: 5
cttctcatca atacctgttc cactgag                                      27

<210> SEQ ID NO 6
<211> LENGTH: 27
<212> TYPE: DNA
<213> ORGANISM: Artificial
<220> FEATURE:
<223> OTHER INFORMATION: Amorce/primer

<400> SEQUENCE: 6
atcaggacaa ctgacttgtc agatgag                                      27

<210> SEQ ID NO 7
<211> LENGTH: 20
<212> TYPE: DNA
<213> ORGANISM: Artificial
<220> FEATURE:
<223> OTHER INFORMATION: Amorce/primer

<400> SEQUENCE: 7
cacatcacaa ccctcattgc                                              20

<210> SEQ ID NO 8
<211> LENGTH: 20
<212> TYPE: DNA
<213> ORGANISM: Artificial
<220> FEATURE:
<223> OTHER INFORMATION: Amorce/primer

<400> SEQUENCE: 8
cgaagtccag ctccagtttc                                              20

<210> SEQ ID NO 9
<211> LENGTH: 20
<212> TYPE: DNA
<213> ORGANISM: Artificial
<220> FEATURE:
<223> OTHER INFORMATION: Amorce/primer

<400> SEQUENCE: 9
aaagcttgcg gtgaggtaga                                              20
```

-continued

```
<210> SEQ ID NO 10
<211> LENGTH: 20
<212> TYPE: DNA
<213> ORGANISM: Artificial
<220> FEATURE:
<223> OTHER INFORMATION: Amorce/primer

<400> SEQUENCE: 10
cttgtcaagg agcgacttcc                                          20

<210> SEQ ID NO 11
<211> LENGTH: 20
<212> TYPE: DNA
<213> ORGANISM: Artificial
<220> FEATURE:
<223> OTHER INFORMATION: Amorce/primer

<400> SEQUENCE: 11
ctccgtgaga gctggaaaac                                          20

<210> SEQ ID NO 12
<211> LENGTH: 20
<212> TYPE: DNA
<213> ORGANISM: Artificial
<220> FEATURE:
<223> OTHER INFORMATION: Amorce/primer

<400> SEQUENCE: 12
cgtttccgtt tatggctgtt                                          20

<210> SEQ ID NO 13
<211> LENGTH: 20
<212> TYPE: DNA
<213> ORGANISM: Artificial
<220> FEATURE:
<223> OTHER INFORMATION: Amorce/primer

<400> SEQUENCE: 13
ccccaaccag acctctctgt                                          20

<210> SEQ ID NO 14
<211> LENGTH: 20
<212> TYPE: DNA
<213> ORGANISM: Artificial
<220> FEATURE:
<223> OTHER INFORMATION: Amorce/primer

<400> SEQUENCE: 14
tctgatggct caaacacagc                                          20

<210> SEQ ID NO 15
<211> LENGTH: 20
<212> TYPE: DNA
<213> ORGANISM: Artificial
<220> FEATURE:
<223> OTHER INFORMATION: Amorce/primer

<400> SEQUENCE: 15
tgggcagata tgacctgaca                                          20

<210> SEQ ID NO 16
<211> LENGTH: 20
<212> TYPE: DNA
<213> ORGANISM: Artificial
<220> FEATURE:
<223> OTHER INFORMATION: Amorce/primer
```

```
<400> SEQUENCE: 16
ttacgaagtg cccctgtacc                                            20

<210> SEQ ID NO 17
<211> LENGTH: 20
<212> TYPE: DNA
<213> ORGANISM: Artificial
<220> FEATURE:
<223> OTHER INFORMATION: Amorce/primer

<400> SEQUENCE: 17
caccaagcgt gtgaagaaga                                            20

<210> SEQ ID NO 18
<211> LENGTH: 20
<212> TYPE: DNA
<213> ORGANISM: Artificial
<220> FEATURE:
<223> OTHER INFORMATION: Amorce/primer

<400> SEQUENCE: 18
cctcagcctt gctaaacagg                                            20

<210> SEQ ID NO 19
<211> LENGTH: 22
<212> TYPE: DNA
<213> ORGANISM: Artificial
<220> FEATURE:
<223> OTHER INFORMATION: Amorce/primer

<400> SEQUENCE: 19
tccaacagcg aactggtaca ga                                         22

<210> SEQ ID NO 20
<211> LENGTH: 19
<212> TYPE: DNA
<213> ORGANISM: Artificial
<220> FEATURE:
<223> OTHER INFORMATION: Amorce/primer

<400> SEQUENCE: 20
gcatgcagta gcggcctttt                                            19

<210> SEQ ID NO 21
<211> LENGTH: 20
<212> TYPE: DNA
<213> ORGANISM: Artificial
<220> FEATURE:
<223> OTHER INFORMATION: Amorce/primer

<400> SEQUENCE: 21
tgcaaccaat ttggaaaaca                                            20

<210> SEQ ID NO 22
<211> LENGTH: 20
<212> TYPE: DNA
<213> ORGANISM: Artificial
<220> FEATURE:
<223> OTHER INFORMATION: Amorce/primer

<400> SEQUENCE: 22
ttcatgggtt cccagaagag                                            20

<210> SEQ ID NO 23
<211> LENGTH: 20
```

```
<212> TYPE: DNA
<213> ORGANISM: Artificial
<220> FEATURE:
<223> OTHER INFORMATION: Amorce/primer

<400> SEQUENCE: 23
gcagccagaa cagaagttcc                                            20

<210> SEQ ID NO 24
<211> LENGTH: 20
<212> TYPE: DNA
<213> ORGANISM: Artificial
<220> FEATURE:
<223> OTHER INFORMATION: Amorce/primer

<400> SEQUENCE: 24
atcaggggtg tctgcatagg                                            20

<210> SEQ ID NO 25
<211> LENGTH: 20
<212> TYPE: DNA
<213> ORGANISM: Artificial
<220> FEATURE:
<223> OTHER INFORMATION: Amorce/primer

<400> SEQUENCE: 25
ctcctggcgt ctaaatgagc                                            20

<210> SEQ ID NO 26
<211> LENGTH: 20
<212> TYPE: DNA
<213> ORGANISM: Artificial
<220> FEATURE:
<223> OTHER INFORMATION: Amorce/primer

<400> SEQUENCE: 26
ggagcaatcc tttcattcca                                            20

<210> SEQ ID NO 27
<211> LENGTH: 23
<212> TYPE: DNA
<213> ORGANISM: Artificial
<220> FEATURE:
<223> OTHER INFORMATION: Amorce/primer

<400> SEQUENCE: 27
atgggtgtga caccaacgcg gcc                                        23

<210> SEQ ID NO 28
<211> LENGTH: 23
<212> TYPE: DNA
<213> ORGANISM: Artificial
<220> FEATURE:
<223> OTHER INFORMATION: Amorce/primer

<400> SEQUENCE: 28
gtagatacac tgggcccgct ggg                                        23

<210> SEQ ID NO 29
<211> LENGTH: 20
<212> TYPE: DNA
<213> ORGANISM: Artificial
<220> FEATURE:
<223> OTHER INFORMATION: Amorce/primer

<400> SEQUENCE: 29
```
ggttccacca catcctgact                                              20

<210> SEQ ID NO 30
<211> LENGTH: 20
<212> TYPE: DNA
<213> ORGANISM: Artificial
<220> FEATURE:
<223> OTHER INFORMATION: Amorce/primer

<400> SEQUENCE: 30
tgagcatgcc actaatggag                                              20

<210> SEQ ID NO 31
<211> LENGTH: 20
<212> TYPE: DNA
<213> ORGANISM: Artificial
<220> FEATURE:
<223> OTHER INFORMATION: Amorce/primer

<400> SEQUENCE: 31
tggcactgat ggctttgtaa                                              20

<210> SEQ ID NO 32
<211> LENGTH: 20
<212> TYPE: DNA
<213> ORGANISM: Artificial
<220> FEATURE:
<223> OTHER INFORMATION: Amorce/primer

<400> SEQUENCE: 32
caggtgatct tcccgttgtt                                              20

<210> SEQ ID NO 33
<211> LENGTH: 20
<212> TYPE: DNA
<213> ORGANISM: Artificial
<220> FEATURE:
<223> OTHER INFORMATION: Amorce/primer

<400> SEQUENCE: 33
aaacgcctcc ataacaccag                                              20

<210> SEQ ID NO 34
<211> LENGTH: 20
<212> TYPE: DNA
<213> ORGANISM: Artificial
<220> FEATURE:
<223> OTHER INFORMATION: Amorce/primer

<400> SEQUENCE: 34
aaccagtcac agccaaaacc                                              20

<210> SEQ ID NO 35
<211> LENGTH: 20
<212> TYPE: DNA
<213> ORGANISM: Artificial
<220> FEATURE:
<223> OTHER INFORMATION: Amorce/primer

<400> SEQUENCE: 35
ggtccagaga ccacaccact                                              20

<210> SEQ ID NO 36
<211> LENGTH: 20
<212> TYPE: DNA
<213> ORGANISM: Artificial

```
<220> FEATURE:
<223> OTHER INFORMATION: Amorce/primer

<400> SEQUENCE: 36
cctctgggga aagaatcctc                                              20

<210> SEQ ID NO 37
<211> LENGTH: 26
<212> TYPE: DNA
<213> ORGANISM: Artificial
<220> FEATURE:
<223> OTHER INFORMATION: Amorce/primer

<400> SEQUENCE: 37
gggcaagttc cgtgggcatc atgttg                                       26

<210> SEQ ID NO 38
<211> LENGTH: 31
<212> TYPE: DNA
<213> ORGANISM: Artificial
<220> FEATURE:
<223> OTHER INFORMATION: Amorce/primer

<400> SEQUENCE: 38
ccagtaactc agctactctt tgtggctttc t                                 31

<210> SEQ ID NO 39
<211> LENGTH: 26
<212> TYPE: DNA
<213> ORGANISM: Artificial
<220> FEATURE:
<223> OTHER INFORMATION: Amorce/primer

<400> SEQUENCE: 39
gctcctcggc tttgacagag tgcaag                                       26

<210> SEQ ID NO 40
<211> LENGTH: 30
<212> TYPE: DNA
<213> ORGANISM: Artificial
<220> FEATURE:
<223> OTHER INFORMATION: Amorce/primer

<400> SEQUENCE: 40
gcatttgtgt ccaggtcctc catgatgtgt                                   30

<210> SEQ ID NO 41
<211> LENGTH: 20
<212> TYPE: DNA
<213> ORGANISM: Artificial
<220> FEATURE:
<223> OTHER INFORMATION: Amorce/primer

<400> SEQUENCE: 41
agctttgtgg gggagaaagt                                              20

<210> SEQ ID NO 42
<211> LENGTH: 20
<212> TYPE: DNA
<213> ORGANISM: Artificial
<220> FEATURE:
<223> OTHER INFORMATION: Amorce/primer

<400> SEQUENCE: 42
atccatggca ggaagtcaag                                              20
```

<210> SEQ ID NO 43
<211> LENGTH: 20
<212> TYPE: DNA
<213> ORGANISM: Artificial
<220> FEATURE:
<223> OTHER INFORMATION: Amorce/primer

<400> SEQUENCE: 43
ctgctgacga tgatgaagga                                              20

<210> SEQ ID NO 44
<211> LENGTH: 20
<212> TYPE: DNA
<213> ORGANISM: Artificial
<220> FEATURE:
<223> OTHER INFORMATION: Amorce/primer

<400> SEQUENCE: 44
ctcccagcaa ggacagaaac                                              20

<210> SEQ ID NO 45
<211> LENGTH: 20
<212> TYPE: DNA
<213> ORGANISM: Artificial
<220> FEATURE:
<223> OTHER INFORMATION: Amorce/primer

<400> SEQUENCE: 45
gagaactcac tggccgagac                                              20

<210> SEQ ID NO 46
<211> LENGTH: 20
<212> TYPE: DNA
<213> ORGANISM: Artificial
<220> FEATURE:
<223> OTHER INFORMATION: Amorce/primer

<400> SEQUENCE: 46
ctgaagaggc ttccctgatg                                              20

<210> SEQ ID NO 47
<211> LENGTH: 20
<212> TYPE: DNA
<213> ORGANISM: Artificial
<220> FEATURE:
<223> OTHER INFORMATION: Amorce/primer

<400> SEQUENCE: 47
cattctgtct cccccaaaaa                                              20

<210> SEQ ID NO 48
<211> LENGTH: 20
<212> TYPE: DNA
<213> ORGANISM: Artificial
<220> FEATURE:
<223> OTHER INFORMATION: Amorce/primer

<400> SEQUENCE: 48
atgggggtat aagggagctg                                              20

<210> SEQ ID NO 49
<211> LENGTH: 20
<212> TYPE: DNA
<213> ORGANISM: Artificial
<220> FEATURE:
<223> OTHER INFORMATION: Amorce/primer

```
<400> SEQUENCE: 49
tgcagctgga tgactacctg                                             20

<210> SEQ ID NO 50
<211> LENGTH: 20
<212> TYPE: DNA
<213> ORGANISM: Artificial
<220> FEATURE:
<223> OTHER INFORMATION: Amorce/primer

<400> SEQUENCE: 50
gaagctctcc caggacacag                                             20
```

MOLECULAR SIGNATURE REPRESENTATIVE OF DYSFUNCTIONS IN EPIDERMAL HOMEOSTASIS

CROSS-REFERENCE TO PRIORITY/PROVISIONAL APPLICATIONS

This application claims priority under 35 U.S.C. §119 of FR 08/04169, filed Jul. 22, 2008, and of U.S. Provisional Application No. 61/095,360, Sep. 9, 2008, each hereby expressly incorporated by reference and each assigned to the assignee hereof.

BACKGROUND OF THE INVENTION

Technical Field of the Invention

The present invention relates to the field of cosmetics, and more particularly to the field of skin.

The invention resides in the identification by the inventors of 25 genes the modulation kinetics or the degree of modulation of which in the epidermis following a challenge reflects the epidermal homeostasis of the skin and distinguishes between a skin termed "aged" and a skin termed "young".

Description of Background and/or Related and/or Prior Art

The stratum corneum is the superficial layer of the epidermis situated at the interface between the organism and its environment. It is composed of corneocytes, which are anuclear cells resulting from the differentiation of epidermal keratinocytes. Corneocytes are rich in keratins and are surrounded by an impermeable lipid matrix. Because of its protein and lipid composition, the stratum corneum plays an essential role as a cutaneous barrier. It prevents the intrusion of microbiological agents and can preserve the hydration of the skin and thus of the body in general.

All physical or chemical challenges to the integrity of the stratum corneum result in an increase in water loss through the skin. Hence, the topical application of acetone or detergents causing superficial delipidation of the stratum corneum, or tape stripping, substantially increases the transepidermal water loss (Grubauer, G et al, 1989; Kuss, O. et al, 1998; Pinnagoda, J et al, 1990; Tanaka, M. et al, 1997; Zhai H. et al, 1998). Such alterations in fact perturb the overall epidermal homeostasis and induce therein a physiological response which aims to restore the integrity of the barrier function of the stratum corneum. Thus, keratinocytes from the superficial layers of the epidermis activate the extracellular secretion of lipid bodies in order to rapidly provide the skin with a fresh impermeable membrane and thus to reduce the superficial loss of water (Grubauer, G. et al 1987; Menon, G. K., 1985). Further, the proliferation of keratinocytes of the stratum basale is activated to replace cells of the stratum corneum which have been damaged (Proksch E., 1991; Wood, L. C L et al, 1992).

The "transepidermal water loss" (TEWL) measurement is the most routinely used measurement for evaluating the integrity of the stratum corneum's barrier function (Piepkorn, M. et al, 1994). The TEWL is measured using an evaporimeter. This apparatus has a moisture and temperature detector which enables it to measure the water evaporation gradient at the skin surface. However, TEWL measurements are subjected to a number of different factors which limit accuracy. The ambient temperature, hygrometry, air turbulence or pressure at which the apparatus is applied can induce substantial variations in these measurements (Barel A O et al, 1995). The state of stress of the volunteer during the measurements also has a non-negligible influence, and thus a sufficient rest time before taking a reading is advised elsewhere (Van S et al, 1994). Even in regions as alike as the forearm, randomization of the measurements has been shown to be vital, the TEWL being significantly increased on the dominant forearm (Treffel P et al, 1994). In this context, the development of a simple, reliable, reproducible and accurate method for evaluating the state of the epidermal barrier function and as a consequence the dynamics of its homeostatic function would be of particular advantage.

Regarding ageing of the skin and apart from the known consequences of age on the relief of the skin, aged people report many problems. These problems have their origin in an alteration in the barrier function and the epidermal homeostasis of their skin. It is in particular often observed in aged persons that there is a great tendency towards chronic xerosis, characterized by an increased loss of water through the skin. In fact, the stratum corneum of aged skin has a decreased intercellular lipid content compared with young skin, particularly during the winter period. This change in the composition of the stratum corneum perturbs its physico-chemical cutaneous barrier properties. The stratum corneum becomes much more sensitive with age to physical or chemical challenges such as tape stripping or the application of acetone (Ghadially R et al, 1995) and its permeability to medication and in particular to hydrophilic compounds is decreased. Further, the severity of contact allergies is exacerbated on aged skin because of a slower and thus less frequent epidermal turnover (Piaserico S ea, 2004). Finally, the rate of recovery of the barrier function after alteration of the stratum corneum slows down with age, leading to the assumption that the homeostatic function of the epidermis is in dysfunction (Denda, M., 2002; Ghadially, R. et al, 1995; Leveque, J. L., 2001). However, despite these functional perturbations due to skin ageing, it has been shown that the thickness of the stratum corneum in aged persons is equivalent to that of young skin (Lock-Andersen J et al, 1997) with little difference in the constitutive TEWL (Ghadially R et al, 1995). This shows that for ageing, the TEWL is not a complete evaluation of the functionality of the cutaneous barrier and the epidermal homeostasis of the skin of a subject.

In contrast, the majority of clinical studies described up to now have been based on TEWL measurements in order to evaluate the effect of treatments on the cutaneous barrier function or to monitor the return of the epidermis to a normal homeostatic condition after a challenge. During one study aimed at determining the action of various cosmetic treatments on the barrier function of the human epidermis, transcriptomic analysis of the response of the epidermis and TEWL measurements were carried out simultaneously (Marionnet C et al, 2004). This identified reproducible markers which were common to various challenges, as well as markers which were specific to each challenge; however, the TEWL could not supply elements which could compare the cosmetic treatments which were carried out.

Under these conditions, there is a need for pertinent, reproducible and significant markers to be identified which reflect the epidermal homeostasis and which can identify any imbalance in the barrier function due to the epidermal homeostasis of the skin such as the imbalance due to age.

SUMMARY OF THE INVENTION

With this aim, the inventors carried out a comparative transcriptomal study of the kinetics of a return to the epidermal homeostasis of the human skin after alteration of the stratum corneum by tape stripping between healthy young and aged individuals. The expression of several hundred genes varied over time after tape stripping. However, surprisingly and unexpectedly, the inventors observed that 18 particular genes displayed modulation kinetics which were significantly different as a function of age. The inventors also demonstrated that 7 other genes systematically and permanently display a degree of modulation which is significantly different after tape stripping as a function of age.

The 25 genes identified by the inventors thus allows a young skin to be distinguished from an aged skin in response to a challenge, and thus allows the homeostatic capacity of the epidermis of an individual to be evaluated. It is a signature which is representative of the differences in gene expression existing between young human skin and aged skin following an alteration of the barrier function by a challenge.

DEFINITIONS

In the context of the present application, the terms below have the following particular meanings:

Tape stripping: this is a method for producing a physical challenge to the skin, consisting of eliminating corneocytes using an adhesive tape, if necessary repeating detachment of the adhesive strip several times. Tape stripping is termed "controlled" when it only alters the stratum corneum and possibly the superficial layers of the malphigian epidermis without altering the deeper layers of the epidermis.

Epidermal homeostasis: This characterizes the set of epidermal regulation functions which endow it with the capacity to maintain a physiological equilibrium and proper function despite external stresses. Homeostasis of the epidermis is also ensured by its barrier function which in particular can prevent the intrusion of microbiological agents and preserve skin hydration by preventing water loss. This capacity may be excellent or good when, in response to a challenge, the epidermis reacts immediately or rapidly to reconstitute the functional equilibrium; it may be deficient or non-existent when the return to equilibrium is delayed or does not occur. This homeostatic capacity of the skin may thus be complete in the case of a normal young skin, or defective, as in the case of an aged skin or any other types of skin with a functional lack of equilibrium.

Thus, the present invention relates to the use of a novel method for clinical evaluation of the state of the epidermis through deficiencies in its homeostatic function by dint of a study of the level of expression of all or part of the 25 genes identified by the inventors.

DETAILED DESCRIPTION OF BEST MODE AND SPECIFIC/PREFERRED EMBODIMENTS OF THE INVENTION

In a first aspect, the present application relates to a method for evaluating the epidermal homeostasis of the skin of a subject, preferably of a human subject.

In a first implementation, said method comprises the differential analysis of the expression of a gene selected from the group of genes consisting of KRT6B, KRT16 (also known as K16), ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, KRT15 (also known as K15), SPRR1B and GSN in response to a physical or chemical challenge of the stratum corneum.

The 25 genes cited above, namely KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, KRT15, SPRR1B and GSN, are termed the genes of the invention. These genes are not part of the type IL-1 cytokine family.

Thus, the present invention concerns the clinical evaluation of the epidermal homeostasis and identifying its dysfunctions by means of a differential analysis of one or more genes of the invention in response to a challenge, preferably of at least two genes.

Of these 25 genes identified by the inventors, certain thereof have been described as being specific to the epidermis. However, it should be noted that prior to the invention, their modulation kinetics or their degree of modulation in response to a physical or chemical challenge had never been identified as varying as a function of the age of an individual and thus could allow an evaluation of epidermal homeostasis.

Further, of the genes identified by the inventors, certain have never been described as being involved in any manner in epidermal homeostasis. These are the genes ESRRA, CBX3, TRIO, TCRB, PRRG2, ICP22BP, GPX3, GBA, BPGM, SMT3H2, LGALS2, DOC1 and GSN. These genes are particularly preferred in the context of the present invention.

In accordance with one implementation, said method comprises a step for challenging the stratum corneum on a region of the skin of an individual then determining:

the kinetics of modulation of the expression of at least one gene selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG; or the degree of modulation of the expression of at least one gene selected from the group consisting of S100A8, S100A9, S100A2, S100A7, K15, SPRR1B and GSN;

in the epidermis corresponding to the challenged region, and a step for comparing the observed kinetics or the degree of modulation with the reference kinetics or the reference level for the modulation of the expression of the selected gene. Preferably, at least two different genes are selected, for example two genes from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG; or two genes from the group consisting of S100A8, S100A9, S100A2, S100A7, K15, SPRR1B and GSN; or at least one gene form the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG, and at least one gene from the group consisting of, S100A9, S100A2, S100A7, K15, SPRR1B and GSN.

In accordance with another implementation, said method comprises comparing modulation kinetics for expression of at least one gene selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG in the epidermis corresponding to a region of the skin after a challenge of the stratum corneum, or comparing the degree of modification of the expression of at least one gene selected from the group consisting of S100A8, S100A9, S100A2, S100A7, KRT15, SPRR1B and GSN in the epidermis corresponding to a region of the skin after a challenge of the stratum corneum, said comparison being carried out with respect to the reference kinetics or the reference level for the modulation of expression of the selected gene. Preferably two distinct genes are selected.

Said subject or individual is a human being, preferably at least 20 years of age, and more particularly at least 40 years of age, preferably at least 60 years of age. This person may be male or female. The skin or epidermis of this subject or individual referred to herein may correspond to any region of the body; preferably, it is the skin or epidermis located on one of the limbs, and in particular the skin or epidermis of the arms, preferably the forearms.

The term "differential analysis of the expression of a given gene" means an analysis of the differences between the expression (or the expression kinetics or the level of expression) of a gene in a region of skin which has been challenged with respect to a region of skin of the same individual which has not been challenged.

Similarly, the term "modulation kinetics" or "degree of modulation" of a given gene means the difference between the expression kinetics or level of expression of the gene in challenged skin and that in unchallenged skin. The challenged and unchallenged skin is that of the same individual.

Preferably, the challenged and unchallenged skin zones are zones of skin which are equivalent in terms of position and function; as an example, it may concern zones of skin located on the left and right limbs, at equivalent locations, in particular the inside of the forearm.

In accordance with a preferred implementation of the method of the invention, the modulation in expression of the selected gene or genes is/are normalized with respect to the expression of at least one gene selected from the group consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS in the epidermis corresponding to the challenged region.

Preferably, normalization is carried out using at least one gene from the group consisting of RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS.

The inventors have demonstrated that the level of expression of said genes is not only constant over the time following the challenge, but also similar regardless of the age of the individual; as a consequence, the level of expression of these genes is completely independent of the epidermal homeostasis. The level of expression of these genes is thus adapted to carry out normalization of the kinetics or the level of expression of a selected gene of the present invention. The 19 genes cited above may qualify as "housekeeping genes".

In the method of the present invention, the challenge to the stratum corneum which is produced on the skin is a physical or chemical challenge. In accordance with a preferred implementation illustrated more particularly in the experimental section of the present application, the challenge is carried out by "tape stripping". In other implementations, the challenge may be chemical and, for example, consist of applying acetone, a delipidation agent (for example SLS, SDS, etc) or an abrasive acidic or basic chemical agent. The challenge may also be produced using a mechanical method such as abrasion or using microneedles; it may also be produced by a physical method such as heat.

Other conventional methods for altering the stratum corneum are well known to the skilled person in the field of the invention.

Preferably, the challenge to the stratum corneum made in the methods of the invention entrains a major alteration of the stratum corneum. More particularly preferably, the vast majority of the stratum corneum is damaged or completely removed over the zone which is challenged.

In order to limit the discomfort to the individual, however, the zone which is challenged may be limited to a few square centimeters or even less. Preferably, the minimum diameter of the zone is 3 mm.

Preferably, the physical or chemical challenge to the stratum corneum is limited to the stratum corneum and does not damage the other layers of the epidermis, nor the dermis. In the experimental section of this application, we describe carrying out controlled tape stripping which means that only the stratum corneum is altered. The superficial layers of the malphigian epidermis may possibly be affected, but preferably the challenge is controlled to avoid affecting the deeper layers of the epidermis.

For the various genes of the invention, in certain implementations of the methods of the invention, mention is made of the reference kinetics or the reference level for gene expression modulation. These reference kinetics or reference level correspond to modulation of the expression of a gene of the invention which is observed after physical or chemical challenge of the skin and characterizing a normal epidermal homeostasis, i.e., a normal barrier function for the epidermis such as that found in general for the skin of young subjects.

Preferably, the reference kinetics and/or the reference level for modulation of the genes of the invention correspond to those observed normally for the skin of a subject approximately 25 years of age. The term "normally" means the kinetics or the level corresponding to the mean plus or minus 10% of the levels or kinetics of at least five, preferably ten or even at least twenty or even a hundred individuals approximately 25 years of age.

These reference kinetics and/or reference level for the modulation of a gene of the invention may be determined for young volunteers, preferably less than 25 years of age, as a function of the challenge made. The volunteers are preferably more than 18 years of age.

The experimental section of the present application demonstrates the determination of the kinetics and the degree of modulation of the 25 genes of the invention in individuals of 25 years of age (±4 years); the kinetics and the degree of modulation observed may constitute, in the context of the present invention, reference kinetics and a reference degree for modulation of the genes of the invention in response to tape stripping.

In contrast, it is possible to define the reference kinetics and/or the reference level for modulation of the genes of the invention with respect to the modulation of said genes in individuals with skin termed aged, i.e., where the epidermal homeostasis or homeostatic barrier function is altered.

As an example, in certain implementations of the methods of the invention, the reference kinetics or the reference level corresponds to the kinetics or the degree of modulation of expression of said gene normally observed for the skin of a subject of approximately 60 years of age or more. The term "normally" means "mean" observed kinetics or modulations, i.e., for at least 5, preferably at least 10, or even 20 or 100 individuals more than 60 years of age.

It will be recalled that in the context of the present invention, particularly preferred genes from the 25 genes turned up by the inventors are the genes ESRRA, CBX3, TRIO, TCRB, PRRG2, ICP22BP, GPX3, GBA, BPGM, SMT3H2, LGALS2, DOC1 and GSN.

For this reason, in accordance with preferred implementations of the methods of the invention, they comprise comparing the kinetics of modulation of the expression of at least one gene selected from the group consisting of ESRRA, CBX3, TRIO, TCRB, PRRG2, ICP22BP, GPX3, GBA, BPGM, SMT3H2, LGALS2 and DOC1 or comparing the degree of modulation of expression of the gene GSN.

The present inventors have demonstrated that in response to a physical or chemical challenge to the stratum corneum, the kinetics and/or degree of modulation of these 25 genes would differ as a function of the homeostatic capacity of the epidermis of the skin under examination, which thus constitutes a signature of the differences in gene expression. However, the modulations may be different depending on the individuals; further, other factors may lead to modulation of a gene of the invention without said modulation being necessarily linked to the epidermal homeostasis.

Under these conditions, the methods of the invention are preferably implemented by carrying out a differential analysis or comparison of the degrees or kinetics of the modulation of at least two different genes selected from group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, KRT15, SPRR1B and GSN. Preferably, at least 3 different genes are selected and their modulation is monitored in response to a challenge of the stratum corneum. The combination of at least two genes or more may in particular be selected from the group of genes consisting of ESRRA, CBX3, TRIO, TCRB, PRRG2, ICP22BP, GPX3, GBA, BPGM, SMT3H2, LGALS2, DOC1 and GSN. In accordance with other preferred implementations, at least five different genes are selected, preferably at least 7 or at least 10, 12, 15 or 20, or the 25 genes.

Combinations which are more particularly envisaged in the context of the present invention are as follows: at least one gene from genes KRT6B and KRT16 combined with at least one gene from the group of genes consisting of ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG and at least one gene from the genes S100A8, S100A9, S100A2, S100A7, KRT15, SPRR1B and GSN.

Preferably, at least two genes are selected. In accordance with a particularly preferred implementation envisaged in the context of the present invention, at least one of the genes of the combination is selected from the group of genes consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG and at least one gene of the combination is selected from the group consisting of S100A8, S100A9, S100A2, S100A7, K15, SPRR1B and GSN. In accordance with another implementation, at least one gene is selected from the group consisting of ESRRA, CBX3, TRIO, TCRB, PRRG2, ICP22BP, GPX3, GBA, BPGM, SMT3H2, LGALS2 and DOC1 and at least one other gene is selected from S100A8, S100A9, S100A2, S100A7, K15, SPRR1B and GSN.

In accordance with other cases envisaged by the present invention, at least three genes are selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG and at least two genes are selected from the group consisting of S100A8, S100A9, S100A2, S100A7, K15, SPRR1B and GSN, or at least four genes from the first group and at least three genes from the second group.

Preferably, in the context of the methods of the invention, the differential analysis, the comparison of the modulation kinetics and/or the comparison of the degrees of modulation are carried out in the 72 hours following the chemical or physical challenge, in particular when said challenge is tape stripping. In fact, it is during this time interval that the inventors have established the largest differences between young and aged skin and thus reflect the dysfunctions of the epidermal homeostasis. Preferably, the differential analyses or comparisons mentioned above are carried out in the 36 hours following the chemical or physical challenge.

As explained in the experimental section of the application, the inventors have also noticed that the most significant differences were observed 6 hours and 30 hours following chemical or physical challenge of the stratum corneum.

Under these conditions, for the genes S100A8, S100A9, S100A2, S100A7, K15, SPRR1B and GSN, the differential analysis or comparison of the degree of modulation is preferably carried out 6 hours or 30 hours following the challenge, or successively 6 and 30 hours following the challenge. This analysis or comparison may otherwise be carried out at any time, preferably in the 36 hours following challenge of the stratum corneum.

For the genes selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG, the differential analysis or modulation kinetics for expression of the gene is preferably determined 6 hours and 30 hours after the physical or chemical challenge.

The various methods of the present invention necessitate determining the modulation of the expression of at least one gene selected from the 25 genes of the invention. Gene expression is preferably quantified by analysis of messenger RNA (mRNA) transcribed in the epidermis. The transcribed mRNA is quantified, for example, using the Northern blot, dot blot, RT-PCR, DNA array hybridization, the SAGE method or using microfluidic chips. Other techniques which can quantify mRNA may clearly be used. All of these techniques are known to the skilled person.

As an example, for RT-PCR analysis of gene expression primers, could be used having the following sequences illustrated in Table A (sequences of sense (S) and antisense (AS) primers)).

TABLE A

| ESRRA | S: cctatctcagggagggaagg, (SEQ ID No 1) AS: tctccaagtcccactctgct (SEQ ID No 2) |
|---|---|
| CBX3 | S: ttggcagtttaggacctgct, (SEQ ID No 3) AS: gttcttcctggcttttgctg (SEQ ID No 4) |
| KRT6B | S: cttctcatcaatacctgttccactgag, (SEQ ID No 5) AS: atcaggacaactgacttgtcagatgag (SEQ ID No 6) |
| MAP3K5 | S: cacatcacaaccctcattgc, (SEQ ID No 7) AS: cgaagtccagctccagtttc (SEQ ID No 8) |
| TRIO | S: aaagcttgcggtgaggtaga, (SEQ ID No 9) AS: cttgtcaaggagcgacttcc (SEQ ID No 10) |

TABLE A-continued

| | | |
|---|---|---|
| PIK3CD | S: | ctccgtgagagctggaaaac, (SEQ ID No 11) |
| | AS: | cgttteegtttatggctgtt (SEQ ID No 12) |
| TCRB | S: | ccccaaccagacctctctgt, (SEQ ID No 13) |
| | AS: | tctgatggctcaaacacagc (SEQ ID No 14) |
| PRRG2 | S: | tgggcagatatgacctgaca, (SEQ ID No 15) |
| | AS: | ttacgaagtgccctgtacc (SEQ ID No 16) |
| ICP22BP | S: | caccaagcgtgtgaagaaga, (SEQ ID No 17) |
| | AS: | cctcagccttgctaaacagg (SEQ ID No 18) |
| K16 (or KRT16) | S: | tccaacagcgaactggtacaga, (SEQ ID No 19) |
| | AS: | gcatgcagtagcggcctttt (SEQ ID No 20) |
| GPX3 | S: | tgcaaccaatttggaaaaca, (SEQ ID No 21) |
| | AS: | ttcatgggttcccagaagag (SEQ ID No 22) |
| GBA | S: | gcagccagaacagaagttcc, (SEQ ID No 23) |
| | AS: | atcaggggtgtctgcatagg (SEQ ID No 24) |
| BPGM | S: | ctcctggcgtctaaatgagc, (SEQ ID No 25) |
| | AS: | ggagcaatcctttcattcca (SEQ ID No 26) |
| NID1 | S: | atgggtgtgacaccaacgcggcc, (SEQ ID No 27) |
| | AS: | gtagatacactgggcccgctggg (SEQ ID No 28) |
| SMT3H2 | S: | ggttccaccacatcctgact, (SEQ ID No 29) |
| | AS: | tgagcatgccactaatggag (SEQ ID No 30) |
| LGALS2 | S: | tggcactgatggctttgtaa, (SEQ ID No 31) |
| | AS: | caggtgatcttcccgttgtt (SEQ ID No 32) |
| DOC1 | S: | aaacgcctccataacaccag, (SEQ ID No 33) |
| | AS: | aaccagtcacagccaaaacc (SEQ ID No 34) |
| PRKCG | S: | ggtccagagaccacaccact, (SEQ ID No 35) |
| | AS: | cctctggggaaagaatcctc (SEQ ID No 36) |
| S100A8 | S: | gggcaagttccgtgggcatcatgttg, (SEQ ID No 37) |
| | AS: | ccagtaactcagctactctttgtggctttct (SEQ ID No 38) |
| S100A9 | S: | gctcctcggctttgacagagtgcaag, (SEQ ID No 39) |
| | AS: | gcatttgtgtccaggtcctccatgatgtgt (SEQ ID No 40) |
| S100A2 | S: | agctttgtgggggagaaagt, (SEQ ID No 41) |
| | AS: | atccatggcaggaagtcaag (SEQ ID No 42) |
| S100A7 | S: | ctgctgacgatgatgaagga, (SEQ ID No 43) |
| | AS: | ctcccagcaaggacagaaac (SEQ ID No 44) |
| KRT15 (or K15) | S: | gagaactcactggccgagac, (SEQ ID No 45) |
| | AS: | ctgaagaggcttccctgatg (SEQ ID No 46) |
| SPRR1B | S: | cattctgtctcccccaaaaa, (SEQ ID No 47) |
| | AS: | atgggggtataagggagctg (SEQ ID No 48) |
| GSN | S: | tgcagctggatgactacctg, (SEQ ID No 49) |
| | AS: | gaagctctcccaggacacag (SEQ ID No 50) |

It is also possible to quantify the level of transcription of the genes by analysis of the degree of translation, thereby quantifying the proteins produced. Appropriate techniques in this regard are also well known to the skilled person. As a consequence, the molecular signature identified by the inventors is also traduced by the amount of proteins coded by the 25 genes of the invention.

The degree of transcription of the genes of the invention is analyzed in the epidermis under the stratum corneum which has been challenged. To this end, samples of epidermis or skin are taken, for example using the method described by Marionnet C et al, 2003 (samples using a dermatome, which is an instrument which can remove very fine strips of skin a few tens of millimeters thick) or many other removal methods (biopsies, punch, keratome or microkeratome, etc). As described above, the 25 genes of the invention thus constitute a molecular signature for the skin, representing the differences in gene expression existing between young human skin and aged human skin following an alteration in the barrier function by a chemical or physical challenge such as tape stripping. This molecular signature thus allows the homeostasic function of human skin to be evaluated.

Thus, the present invention also pertains to the use of a gene expression analysis of all or a portion of the genes, and preferably of at least two genes, selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG and from S100A8, S100A9, S100A2, S100A7, K15, SPRR1B and GSN, with the aim of diagnosing the homeostatic function of the skin, the level of expression following tape stripping of all or part of these genes after a few hours, preferably 06 h or 30 h, being characteristic of the age of the individual or deficiencies in its homeostatic function.

The technique consists of monitoring, after a few hours, preferably 6 h and/or 30 h, the expression of all or part of the genes from list 1 consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG and the genes from list 2 consisting of S100A8, S100A9, S100A2, S100A7, K15, SPRR1B and GSN using any technique for quantifying the expression of mRNA such as Northern blot, dot blot, RT-PCR, DNA array hybridization, the SAGE method, or using microfluidic chips, etc.

The transcriptomic study of these genes is rendered possible by means of standardization using the housekeeping genes identified and listed in list 3, consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS.

As an example, the primers could be used for analysis by RT-PCR of the gene expression corresponding to those illustrated in Table A.

The present invention also concerns diagnostic methods which can identify deficiencies in the epidermal homeostasis of a human skin, such as the deficiencies observed for an aged skin. Such a diagnosis of the condition of the epidermis of a human individual comprises evaluating the homeostatic function or epidermal homeostasis of the skin of said individual using one of the methods described above. By this method, the genetic signature identified by the inventors means that individuals can be detected for whom the barrier function and/or homeostasis of the skin has deficiencies, thereby weakening it. Such a diagnosis can thus lead to the conclusion of the necessity of treating the skin to reinforce the homeostasis and/or the epidermal barrier function and thus to preserve them. In fact, a deficiency in the epidermal homeostasis is synonymous with fragilisation of the skin and with discomforts such as those suffered by aged persons.

Preferably, the diagnosis is carried out on an individual of at least 20, or even at least 30, 40, 50, 55 or 60 years of age. The diagnostic method of the present invention may also be appropriate for persons who have undergone major treatments which may have modified the epidermal homeostasis, in particular topical treatments.

In accordance with this diagnostic method of the invention, the diagnosed skin is qualified as "aged skin" if the differential analysis of the expression of at least one, preferably at least two of the genes selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN differs by more than 50% from the mean modulation normally observed for skin of a subject approximately 25 years of age, preferably 30 hours after physical or chemical challenge. The mean modulation normally observed for an individual of approximately 25 years of age corresponds to the "reference" modulation.

The difference in expression between a gene of the invention and the mean modulation is calculated as follows: [intensity of observed modulation−intensity of reference modulation]/intensity of reference modulation. As explained in the sections above, the intensity of modulation is normalized using the level of expression of genes termed housekeeping genes which are selected from the group of genes consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS, preferably selected from RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS.

Preferably, the differential analysis of the expression of at least one of the genes differs by more than 60% from the reference modulation, or even by more than 90% from the reference modulation.

Preferably, in order to provide a reliable diagnosis, it is preferable to analyze the differences in modulation of at least 2, 3 or even 5 genes from among the genes mentioned above.

In accordance with more particularly preferred implementations, it is concluded that a skin has "aged skin" behavior if at least 8, 10, 12 or 15 of the genes of the invention present a greatly different modulation from the reference modulation, or the 25 genes of the invention.

In another aspect, the present invention pertains to the use of an analysis of the expression of the genes described in the present invention to evaluate the anti-ageing effect of a product (active ingredient, molecule, natural extract, combination of active ingredients) but also of a procedure (light, injection, oral ingestion), alone or as a combination, by testing their capacity to normalize the response of the epidermis to a challenge. The benefit of such a product or anti-ageing procedure is characterized by its capacity to:

i) accelerate the kinetics of modulation of the genes KRT6B and KRT16 after tape stripping in aged individuals; and/or to ii) inhibit the induction at 30 h of all or part of the genes ESRRA, CBX3, MAP3K5, TRIO, PIK3CD, TCRB, PRRG2, ICP22BP, GPX3, GBA, BPGM, NID1, SMT3H2, LGALS2, DOC1, PRKCG after tape stripping in aged individuals; and/or iii) normalize the intensity of modulation of the genes S100A8, S100A9, S100A2, S100A7, KRT15, SPRR1B and GSN in aged individuals.

Thus, the present invention also concerns a process for determining the effectiveness of a treatment of the epidermis of an individual, comprising evaluating the homeostatic function of the skin before and after treatment using a method as described above. In fact, the signature representative of the differences in gene expression following an alteration of the stratum corneum may be used to determine the effectiveness of a treatment of the epidermis. To this end, said signature has to be determined before and after carrying out a treatment the effectiveness of which is to be determined, preferably on an aged skin.

Preferably, the procedure for determining the effectiveness of a treatment is carried out on skin of an individual aged at least 20 or 30 years, preferably at least 40 years, or even at least 50 or 60 years.

By dint of this method, it is thus possible to determine the capacity of certain treatments, especially cosmetic compositions for topical application to the skin or food supplements or certain cosmetic procedures using instruments (light, injection, iontophoresis) to reinforce the epidermal homeostasis, and thus to determine their capacity to "rejuvenate" the skin. The term "rejuvenation" of the skin means improving the epidermal homeostasis such that the behavior of the skin in response to a challenge returns to that which is closer to the behavior of a young skin in response to the same challenge.

The present invention also concerns a method for screening active ingredients for their beneficial action on the epidermal homeostasis of the human epidermis, comprising evaluating the epidermal homeostasis of the skin of an individual using a method in accordance with that described above, before and after application of the molecule to be screened.

As detailed above, the representative signature discovered by the inventors can in fact determine the improvement in the epidermal homeostasis and/or the barrier function of aged skin. Such an improvement is precisely characterized by modulation kinetics or a degree of modulation after treatment which is closer to the modulation kinetics or the degree of modulation observed from the skin of a young subject.

The present invention also pertains to a method for testing treatments for their beneficial effect on human epidermal homeostasis, comprising evaluating the epidermal homeostasis of the skin of an individual by a method as described above, before and after application of the treatment to be tested. The use of the molecular signature defined by the inventors for this purpose is identical to that detailed above for the method for screening molecules for their beneficial action on epidermal homeostasis.

Preferably, a test method as described is carried out on an aged individual at least 20 or 30 years of age, preferably at least 40 years of age, and more preferably at least 50 or even 60 years of age.

Examples of treatments which may thus be evaluated for their positive action on the epidermal homeostasis are the local application of electromagnetic waves or of any chemical composition, product or molecule or the injection or ingestion of a chemical composition, product or molecule. Preferably, it is a local topical treatment.

The term "product" means both an ingredient or an active ingredient in the more or less purified form, in particular a chemical molecule having an intrinsic activity in vitro or in vivo, and a formulation comprising one or more of said ingredients and a support and adjuvants adapted to the envisaged application.

In the methods for evaluating the effectiveness of the present invention, the treatment or test molecule is considered to be effective if the following is observed:

an acceleration in the modulation kinetics of at least one of genes selected for the group consisting of KRTB6 and KRT16; and/or an inhibition in induction after 30 hours of at least one gene selected from the group consisting of ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG; and/or a modification in the intensity of modulation of at least one gene selected from the group consisting of S100A8, S100A9, S100A2, S100A7, K15, SPRR1B and GSN;

said modification reducing the difference between the observed intensity of modulation and the reference intensity of modulation characteristic of the skin of a subject of about 25 years of age.

Preferably, in order to be evaluated positively, it is preferable that the test treatment or molecule involves a modification in the kinetics or the level of expression of at least two genes, preferably at least 3 genes or even at least 5, 10, 12, 15 or 20 genes from the 25 of the invention, or the 25 genes of the invention.

Preferably again, the acceleration of the kinetics, the inhibition of induction or the modification in the intensity of modulation observed after treatment represents a variation of at least 30% following application of the molecule or treatment. Preferably, the differences observed are even greater, preferably at least 50% or even more, for example at least 60%.

The fact that the inventors have determined a signature representative of epidermal homeostasis means that it is also possible, using the evaluation methods of the present application, to objectify the beneficial action of a treatment, in particular a cosmetic product, for example a cosmetic composition. The evaluation methods described above may in fact be used in a test protocol which means that products which can be qualified as "active as regards the barrier function of the skin" or "having an anti-ageing effect" or a "skin rejuvenating effect" can be discerned.

Further, using this test, it is possible to promote the product to consumers, by emphasizing the results obtained with this product in the methods for evaluating the epidermal homeostasis described in the present invention. The evaluation of the epidermal homeostasis will be based on the study of the expression of the genes of the invention or the proteins encoded by said genes. The present invention thus also provides a method which allows a product to be recommended by indicating its effect in a test protocol constituted by the evaluation method described above. Thus, the invention also pertains to a method for promoting a cosmetic product consisting of reporting an effectiveness, action or property of said product demonstrated by at least one test operated as described above. Such a promotion of the product could be carried out using any communication channel. It could in particular be carried out by the salesperson, directly at the point of sale, on radio or on television, in particular in the context of advertising spots. It could also be carried by the printed press, or any other document, in particular for advertising ends (prospectus). It could also be carried out using the internet, or any other suitable information network. It could also be produced directly on the product, especially on its packaging or any other explanatory notice with which it might be associated.

The present invention also pertains to a kit which can determine good or poor state of the homeostatic function of a skin based on an analysis of the expression of genes constituting the representative signature of the various gene expression differences existing between young human skin and aged skin, following an alteration in the barrier function, for example by tape stripping. Said kit for evaluating the epidermal homeostasis of the skin of a subject comprises a means for producing a physical or chemical challenge of the stratum corneum, a means for taking a sample of the epidermis, which is preferably distinct from the first means, and a means for determining the level of expression of at least one gene selected from the group of genes consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN.

In a preferred implementation of the invention, the kit comprises at least one means for determining the level of expression of at least one gene selected from the group of genes consisting of ESRRA, CBX3, TRIO, TCRB, PRRG2, ICP22BP, GPX3, GBA, BPGM, SMT3H2, LGALS2, DOC1 and GSN.

Preferably, for the reasons mentioned above in the application, the kit comprises means for determining the level of expression of at least 2, 3, 5, 10 or at least 15 different genes selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN and in particular selected from the group consisting of ESRRA, CBX3, TRIO, TCRB, PRRG2, ICP22BP, GPX3, GBA, BPGM, SMT3H2, LGALS2, DOC1 and GSN. The kit may comprise mean for determining the level of expression of the 25 genes of the invention.

Clearly, the kit may comprise supplemental elements, such as various controls, positive or negative. Advantageously, a kit of the invention also comprises a means for determining the level of expression of at least one gene selected from the so-called housekeeping genes, i.e., from the group of genes consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS.

Preferably, a kit of the invention allows two epidermal samples to be taken and allows the level of expression of the selected gene to be determined at least two times, before alteration of the stratum corneum and afterwards, or on a challenged zone and on an unchallenged zone.

The kit of the invention may also include instructions concerning its use and the time to leave between taking the various samples and the alteration of the stratum corneum.

On reading the various method of the invention, it will be clear to the skilled person what such a kit should contain in order to implement said methods.

The present invention also concerns a DNA or RNA array or chip comprising probes which hybridize specifically with cDNA or mRNA of the genes KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN.

A preferred array or chip in the context of the present invention comprises probes hybridizing specifically with cDNA or mRNA of the genes ESRRA, CBX3, TRIO, TCRB, PRRG2, ICP22BP, GPX3, GBA, BPGM, SMT3H2, LGALS2, DOC1 and GSN.

In a particular implementation of the invention, such an array also comprises probes hybridizing with all or part of the cDNA or mRNA of the genes S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS.

The use of said arrays in the context of the various methods of the invention will become apparent to the skilled person on reading the foregoing.

In all the embodiments of this invention, the subject is preferably a human being.

The invention will now be described in more detail using one implementation.

BRIEF DESCRIPTION OF THE DRAWINGS

FIG. 1 shows the expression profile of the 18 genes the modulation kinetics of which between 6 h and 30 h after tape striping which are significantly different depending on the age of the patient;

FIG. 1B) shows the genes, the expression of which increases between 06 h and 30 h in an aged subject but does not vary in a young subject;

FIG. 2 shows the expression profile of 7 genes the modulation intensity of which after tape stripping is significantly different depending on the age of the patient regardless of the time;

Figure 1A:
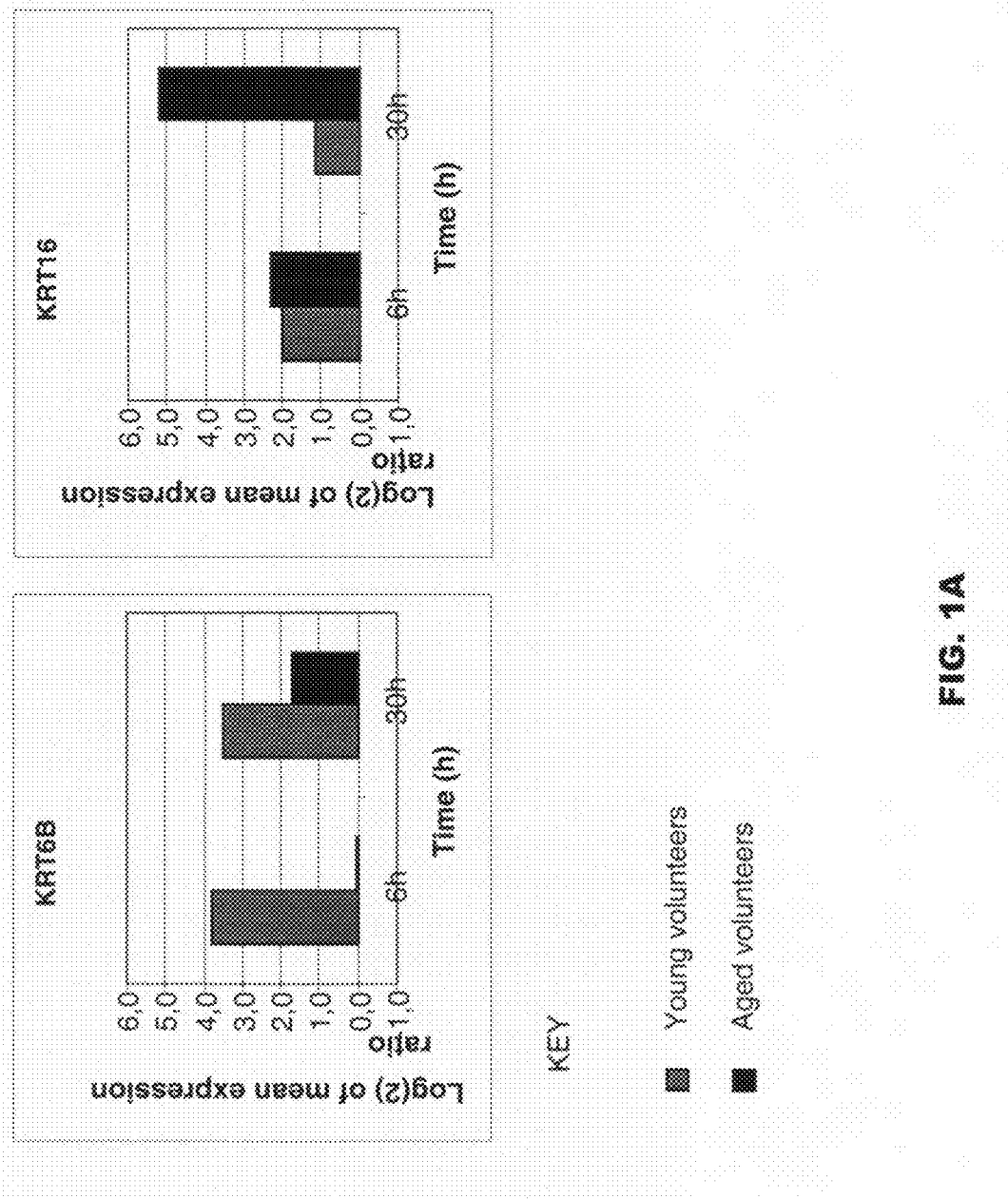
FIG. 1A) shows the genes, the expression of which is modulated at 6 h and at 30 h in the two populations but with kinetics which differ as a function of the population.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Methodology

Healthy male volunteers were recruited in order to participate in a transcriptomic study of more than 4,000 genes which are known to be expressed in the skin.

Recruitment of volunteers: 5 groups of 6 young individuals (25±4 years) and 5 groups of 6 aged individuals (67±4 years) were recruited for this study, following the provision of informed consent.

Alteration of the stratum corneum: Tape stripping was carried out on the inner face of one of their forearms, selected in a randomized manner, until the stratum corneum had been completely removed and the skin had a smooth and shiny appearance (48±7 strips as mean). To this end, a 3M™ Blenderm™ adhesive strip was used (St Paul, Mich., USA). The second forearm did not undergo any treatment.

Epidermal samples: Epidermal samples with a surface area of 1.5 cm×1.5 cm were removed under local anesthesia using a GA360 dermatome (AESCULAP, Melsungen, Germany). The samples were taken from stripped and non-stripped skin. The sample thickness was fixed at 200 µm in accordance with the protocol described by Marionnet et al in 2003, so that only epidermis was removed and to minimize dermal contamination. The samples were taken from both forearms at 02 h, 06 h, 19 h, 30 h, and 72 h after stripping.

RNA extraction: The epidermal samples were placed in Rneasy lysis buffer (Qiagen, Courtaboeuf, France) immediately after taking the sample. The tissue was then ground using a sterile mortar. The tissue lysate was homogenized (QIAshredder, columns, Qiagen, Courtaboeuf, France) and the total RNA was extracted using the Rneasy method (Qiagen, Courtaboeuf, France). DNA was digested to eliminate any genomic contamination (DNAse1, (Qiagen, Courtaboeuf, France). The concentration and purity of the total RNA was determined by measuring the absorbance at 260 nm and 280 nm. The integrity of the RNA was verified by agarose gel electrophoresis after labeling with ethidium bromide. The RNA samples were then precipitated using a highly saline acidic solution (0.1 volume of sodium acetate, 2M, pH4) and ethanol (2.5 volumes of 100% cold ethanol). The samples were stored at −80° C. until use.

Hybridizations on Dermarray cDNA microarray: Aliquots corresponding to 2.5 µg of RNA were removed and precipitated by centrifuging. The RNA were washed, dried then dissolved in RNAse free sterile water. Oligo (dT) 12-18 mers, a mixture of dATP, dTTP and dGTP, AMV reverse transcriptase (Invitrogen SARL, Cergy Pontoise, France) and dCTP labeled with $^{33}$P (Amersham) were used for reverse transcription of the mRNA using the manufacturer's recommendations. The control epidermal samples were reverse transcribed simultaneously with the stripped samples. The probes produced thereby were purified on a biospin6 chromatography column (BioRad, Hercule, Calif., USA). Incorporation of $^{33}$P probes was measured by β-scintillation. The same quantity of probe from the control and stripped epidermal samples was used for the hybridization on DermArray® cDNA microarray membranes (IntegriDerm, Birmingham, Ala., USA), following the recommendation of the manufacturer.

Quantification and correction of signal: The arrays were analyzed using a 16-bit Cyclone Phosphorus Imager scanner which allowed high resolution analysis (Packard Instruments, Perkin-Elmer Life Sciences, Boston, Mass., USA). The images were then imported into Imagene 5 software (Biodiscovery, El Segundo, Calif., USA) to quantify the signal, then the signals were corrected using Genesight software (Biodiscovery, El Segundo, Calif., USA). A local correction of the background noise was carried out and the positive signals were normalized for a control membrane with respect to its control.

Analysis of data: An expression ratio was calculated, dividing the corrected signal for the treated sample by the corrected signal for the control sample. A mean inter-individual ratio was calculated for each time for each gene expressed in at least 50% of the individuals of each group.

Selection of modulated genes in each population: A gene was considered as modulated if its expression was significantly different between the stripped epidermis and the control epidermis (Student test, p<0.05); and if at least 50% of the volunteers of the group had a ratio of more than 2 and none had a ratio of less than 0.5 (induced genes), and conversely for the repressed genes. Finally, genes which had been modulated at least one time over time were selected.

Selection of genes differentially modulated with age: The kinetics of the genes modulated both in young and aged individuals was compared at times 06 h and 30 h (time at which the profiles were most different between young and aged) using a ANOVA two factor test (time factor, age and interaction factor; p<0.05). The genes the expression of which differed significantly with the age of the patient were selected. A significant interaction of the kinetics reflected a temporal offset in gene modulation.

Results:

573 genes were expressed communally in the epidermis in all volunteers, whether young or aged. The expression of some of them varied following tape stripping compared with the control skin (induced or repressed expression) following specific kinetics.

Surprisingly and unexpectedly, the inventors have identified 18 genes the expression kinetics of which after tape stripping was significantly different as a function of the age of the volunteer (Table 1). In particular, the expression of genes KRT6B and KRT16 was induced at 06 h and 30 h in the two populations, but a significant delay in their modulation kinetics was observed in aged individuals (FIG. 1-A). Further, the expression of genes ESRRA, CBX3, MAP3K5, TRIO, PIK3CD, TCRB, PRRG2, ICP22BP, GPX3, GBA, BPGM, NID1, SMT3H2, LGALS2, DOC1, PRKCG increased significantly between 06 h and 30 h following tape stripping in the aged subject, while it remained unchanged over time in the young subject (see examples in FIG. 1-B).

Further, for genes S100A8, S100A9, S100A2, S100A7, KRT15, SPRR1B and GSN (Table 2), the shape of the kinetics was similar between 06 h and 30 h, but there was a significant difference in the modulation intensity of 1.8 log(2) to 3.12 log(2) depending on whether the individual was young or aged (see Examples in FIG. 2).

Figure 3:
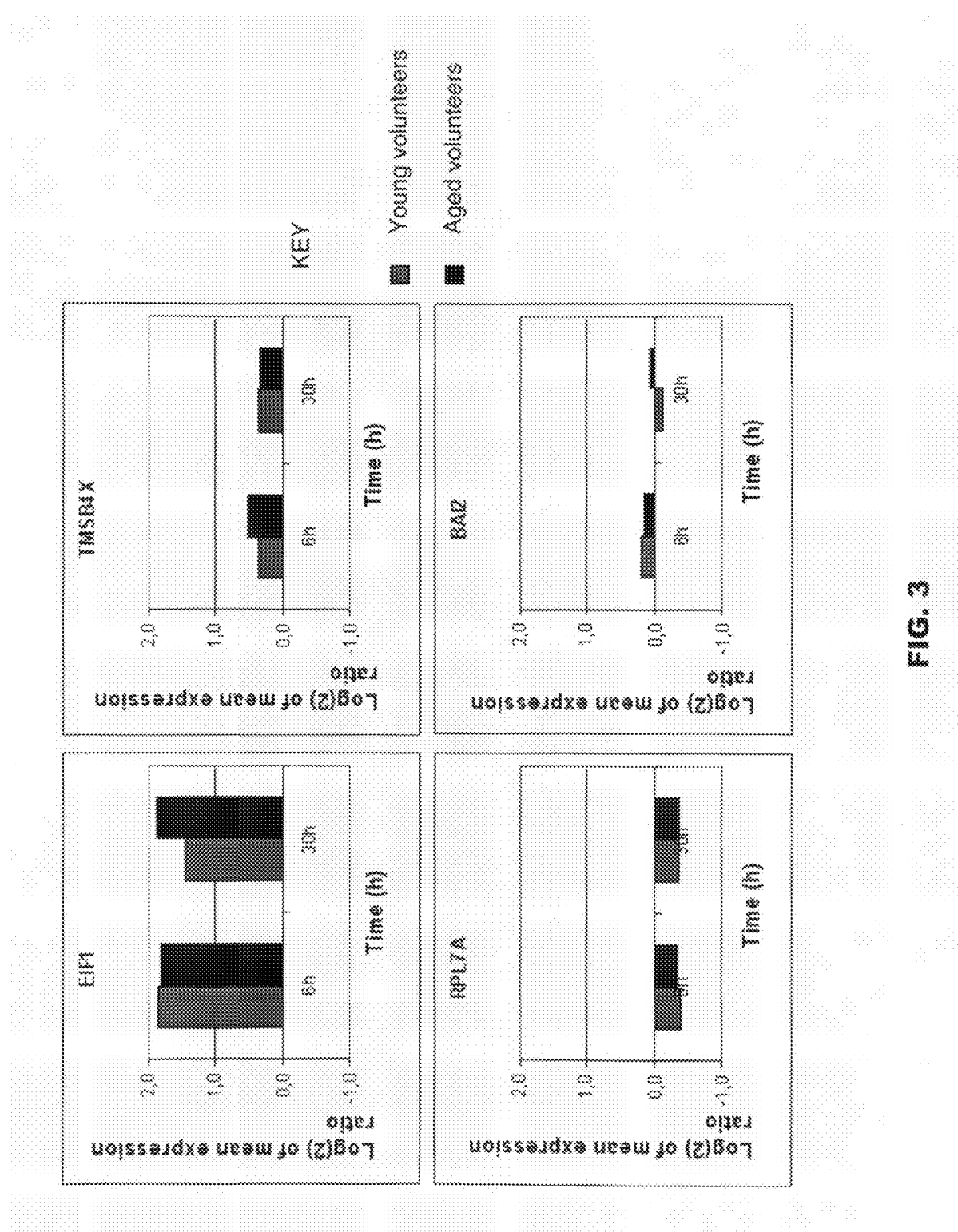
FIG. 3 shows the expression profile of 4 genes the modulation intensity of which after tape stripping does not vary significantly with the age of the patient regardless of the time.

Finally, 109 genes exhibited no significant difference in expression as a function of time or age. These latter may be considered to be housekeeping genes. Only 3 of them, genes S100A10, EIF1 and ACTR1A, had a level of expression which varied following tape stripping, this variation being constant with time. The other genes were not modulated. The inventors selected 19 of them with a similar profile between young and aged. These were mainly ribosomal components known to be housekeeping genes (RPL28, RPL5, RPL35, RPS13, RPS23, RPS16, RPL18, RPS15A, RPL7A, RPS28). The others genes, G3BP1, TMSB4X, HLA-C, DYNLL1, NACA, ARHA, BAI2, UBA52, GNAS, are neither known nor used as housekeeping genes (FIG. 3).

CONCLUSIONS 3 lists of genes of interest have been drawn up:

List 1 (Table 1) shows 18 genes the expression kinetics of which after tape stripping is significantly different between young and aged individuals;

List 2 (Table 2) shows 7 genes the modulation intensity of which differs at all times depending on whether the volunteer is aged or young;

List 3 (Table 3) shows 22 housekeeping genes the expression of which does not vary with the age of the volunteers.

The level of expression of the genes of list 1 and list 2 in aged subjects after tape stripping is the molecular reflection of the dysfunction of the homeostatic function of the epidermis due to age. Analysis of the expression of these genes constitutes a novel solution to the problem of evaluating the effectiveness of active ingredients or anti-ageing protocols which may improve renewal of the epidermal homeostasis and the problem of diagnosis of the age state of the skin. The expression of these genes may be carried out and standardized by dint of the presence of housekeeping genes listed in Table 3.

TABLE 1

List of 18 genes the modulation kinetics of which between 6 h and 30 h following tape stripping is significantly different depending on the age of the patient:

| Accession No. | Symbol of Gene | Name |
|---|---|---|
| AA098896 | ESRRA | estrogen-related_receptor_alpha |
| AA132226 | CBX3 | Human_heterochromatin_protein_HP1Hs-gamma_mRNA,_complete_cds |
| AA150532 | KRT6B (or K16) | keratin_6B |
| AA150828 | MAP3K5 | mitogen-activated_protein_kinase_kinase_kinase_5 |
| AA191348 | TRIO | ESTs,_Highly_similar_to_(defline_not_available_3522970)_[H.sapiens] |
| AA281784 | PIK3CD | phosphoinositide-3-kinase,_catalytic,_delta_polypeptide |
| AA284528 | TCRB | T-cell_receptor,_beta_cluster |
| AA430552 | PRRG2 | proline-rich_Gla_(G-carboxglutamic_acid)_polypeptide_2 |
| AA488979 | ICP22BP | cell_cycle-regulated_factor_(78_kDa) |
| AA596003 | KRT16 | keratin_16_(focal_non-epidermolytic_palmoplantar_keratoderma) |
| AA664180 | GPX3 | glutathione_peroxidase_3_(plasma) |
| AA670347 | GBA | glucosidase,_beta;_acid_(includes_glucosylceramidase) |
| AA678065 | BPGM | 2,3-bisphosphoglycerate_mutase |
| AA709414 | NID1 | nidogen_(enactin) |
| AA775415 | SMT3H2 | SMT3_(suppressor_of_mif_two_3,_yeast)_homolog_2 |
| AA872397 | LGALS2 | lectin,_galactoside-binding,_soluble,_2_(galectin_2) |

TABLE 1-continued

List of 18 genes the modulation kinetics of which between 6 h and 30 h following tape stripping is significantly different depending on the age of the patient:

| Accession No. | Symbol of Gene | Name |
|---|---|---|
| R78607 | DOC1 | deleted_in_oral_cancer_(mouse,_homolog)_1 |
| R89715 | PRKCG | ESTs |

TABLE 2

List of 7 genes the intensity of modulation of which at 6 h and 30 h is significantly different with the age of the patient:

| Accession No. | Symbol of Gene | Name |
|---|---|---|
| AA086471 | S100A8 | S100_calcium-binding_protein_A8_(calgranulin_A) |
| AA864554 | S100A9 | S100_calcium-binding_protein_A9_(calgranulin_B) |
| AA583574 | S100A7 | S100_calcium-binding_protein_A7_(psoriasin_1) |
| AA458884 | S100A2 | S100_calcium-binding_protein_A2 |
| AA878048 | KRT15 (or K15) | keratin_15 |
| AA447684 | SPRR1B | small_proline-rich_protein_1B_(cornifin) |
| H72028 | GSN | gelsolin_(amyloidosis,_Finnish_type) |

TABLE 3

List of 22 housekeeping genes:

| Accession No. | Symbol of Gene | Name |
|---|---|---|
| AA136500 | G3BP1 | ESTs |
| AA423800 | TMSB4X | thymosin,_beta_4,_X_chromosome |
| AA444051 | S100A10 | S100_calcium-binding_protein_A10_(annexin_II_ligand,_calpactin_I,_light_polypeptide_(p11)) |
| AA464246 | HLA-C | major_histocompatibility_complex,_class_I,_C |
| AA464731 | EIF1 | putative_translation_initiation_factor |
| AA486746 | RPL28 | ribosomal_protein_L28 |
| AA496880 | RPL5 | ribosomal_protein_L5 |
| AA625634 | RPL35 | ribosomal_protein_L35 |
| AA629641 | RPS13 | ribosomal_protein_S13 |
| AA634008 | RPS23 | ribosomal_protein_S23 |
| AA644679 | DYNLL1 | dynein,_cytoplasmic,_light_polypeptide |
| AA664241 | NACA | -nascent-polypeptide-associated_complex_alpha_polypeptide |
| AA668301 | RPS16 | ribosomal_protein_S16 |
| AA676955 | ARHA | ras_homolog_gene_family,_member_A |
| AA775874 | RPL18 | ribosomal_protein_L18 |
| AA777034 | BAI2 | ESTs,_Highly_similar_to_BAI_2_[H.sapiens] |
| AA856556 | RPS28 | ribosomal_protein_S28 |
| AA872341 | RPS15A | ribosomal_protein_S15a |
| AA878561 | UBA52 | proteasome_(prosome,_macropain)_subunit,_alpha_type,_7 |
| H23422 | RPL7A | ribosomal_protein_L7a |
| R40850 | ACTR1A | H.sapiens_mRNA_for_alpha-centractin |
| R43581 | GNAS | Human_guanine_nucleotide-binding_protein_G-s,_alpha_subunit_mRNA,_partial_cds |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

REFERENCES

1. Barel, A. O. and Clarys, P.; Study of the stratum corneum barrier function by transepidermal water loss measurements: comparison between two commercial instruments: Evaporimeter and Tewameter; 1995; *Skin Pharmacol;* 8 (186-195)

2. Denda, M.; New strategies to improve skin barrier homeostasis; 1-11-2002; *Adv Drug Deliv Rev,* 54 Suppl 1 (S123-S130)
3. Ghadially, R., Brown, B. E., Sequeira-Martin, S. M., Feingold, K. R., and Elias, P. M.; The aged epidermal permeability barrier. Structural, functional, and lipid biochemical abnormalities in humans and a senescent murine model; 1995; *J Clin Invest;* 95 (2281-2290)
4. Grubauer, G., Feingold, K. R., and Elias, P. M.; Relationship of epidermal lipogenesis to cutaneous barrier function; 1987; *J Lipid Res;* 28 (746-752)
5. Grubauer, G., Feingold, K. R., Harris, R. M., and Elias, P. M.; Lipid content and lipid type as determinants of the epidermal permeability barrier; 1989; *J Lipid Res;* 30 (89-96)
6. Kuss, O. and Diepgen, T. L.; Proper statistical analysis of transepidermal water loss (TEWL) measurements in bioengineering studies; 1998; *Contact Dermatitis;* 39 (64-67)
7. Leveque, J. L.; Quantitative assessment of skin aging; 2001; *Clin Geriatr Med;* 17 (673-89, vi)
8. Lock-Andersen, J., Therkildsen, P., de Fine, Olivarius F., Gniadecka, M., Dahlstrom, K., Poulsen, T., and Wulf, H. C.; Epidermal thickness, skin pigmentation and constitutive photosensitivity; 1997; *Photodermatol Photoimmunol Photomed;* 13 (153-158)
9. Marionnet, C., Bernerd, F., Dumas, A., Verrecchia, F., Mollier, K., Compan, D., Bernard, B., Lahfa, M., Leclaire, J., Medaisko, C., Mehul, B., Seite, S., Mauviel, A., and Dubertret, L.; Modulation of gene expression induced in human epidermis by environmental stress in vivo; 2003; *J Invest Dermatol;* 121 (1447-1458)
10. Menon, G. K., Feingold, K. R., Moser, A. H., Brown, B. E., and Elias, P. M.; De novo sterologenesis in the skin. II. Regulation by cutaneous barrier requirements; 1985; *J Lipid Res;* 26 (418-427)
11. Piaserico, S., Larese, F., Recchia, G. P., Corradin, M. T., Scardigli, F., Gennaro, F., Carriere, C., Semenzato, A., Brandolisio, L., Peserico, A., and Fortina, A. B.; Allergic contact sensitivity in elderly patients; 2004; *Aging Clin Exp Res;* 16 (221-225)
12. Piepkorn, M., Lo, C., and Plowman, G.; Amphiregulin-dependent proliferation of cultured human keratinocytes: autocrine growth, the effects of exogenous recombinant cytokine, and apparent requirement for heparin-like glycosaminoglycans; 1994; *J Cell Physiol;* 159 (114-120)
13. Pinnagoda, J., Tupker, R. A., Agner, T., and Serup, J.; Guidelines for transepidermal water loss (TEWL) measurement. A report from the Standardization Group of the European Society of Contact Dermatitis; 1990; *Contact Dermatitis;* 22 (164-178)
14. Proksch, E., Feingold, K. R., Man, M. Q., and Elias, P. M.; Barrier function regulates epidermal DNA synthesis; 1991; *J Clin Invest;* 87 (1668-1673)
15. Tanaka, M., Zhen, Y. X., and Tagami, H.; Normal recovery of the stratum corneum barrier function following damage induced by tape stripping in patients with atopic dermatitis; 1997; *Br J Dermatol;* 136 (966-967)
16. Treffel, P., Panisset, F., Faivre, B., and Agache, P.; Hydration, transepidermal water loss, pH and skin surface parameters: correlations and variations between dominant and non-dominant forearms; 1994; *Br J Dermatol;* 130 (325-328)
17. Van, Sam, V, Passet, J., Maillols, H., Guillot, B., and Guilhou, J. J.; TEWL measurement standardization: kinetic and topographic aspects; 1994; *Acta Derm Venereol;* 74 (168-170)
18. Wood, L. C., Jackson, S. M., Elias, P. M., Grunfeld, C., and Feingold, K. R.; Cutaneous barrier perturbation stimulates cytokine production in the epidermis of mice; 1992; *J Clin Invest;* 90 (482-487)
19. Zhai, H., Leow, Y. H., and Maibach, H. I.; Human barrier recovery after acute acetone perturbation: an irritant dermatitis model; 1998; *Clin Exp Dermatol;* 23 (11-13)

---

What is claimed is:

1. A method of measuring mRNA transcription in skin in which the stratum corneum been altered by tape stripping, the method comprising the steps of:
   a) altering the stratum corneum of skin of a human subject by tape stripping;
   b) removing a first sample of epidermis from skin of the human subject that has not been altered by tape stripping;
   c) after 6 hours and/or after 30 hours following the tape stripping, removing a second sample of epidermis from skin of the human subject that has been altered by tape stripping; and,
   d) a measuring step consisting of
      measuring the mRNA transcription of at least three genes selected from the group of genes consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN in the samples of epidermis removed from the subject;
      and optionally measuring at least one gene selected from the group consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS in the epidermis of the subject.

2. The method of claim 1, further comprising comparing the modulation kinetics of the expression of at least one gene selected
   from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG in the epidermis corresponding to a region of the skin following physical challenge to the stratum corneum; or
   the degree of modulation of the expression of at least one gene selected from the group consisting of S100A8, S100A9, S100A2, S100A7, K15, SPRR1B and GSN in the epidermis corresponding to a region of the skin after physical challenge of the stratum corneum;
   with reference kinetics or reference level of modulation of the expression of the selected gene,
   wherein at least two distinct genes are selected.

3. The method of claim 2, wherein the modulation of the expression of the selected genes is determined with reference to another region of the skin which has not been subjected to the challenge.

4. The method of claim 2, wherein the modulation of the expression of the selected genes is normalized with respect to the expression of at least one gene selected from the group consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS in the epidermis corresponding to the challenged region.

5. The method of claim 2, wherein the reference kinetics or the reference level corresponds to the kinetics or the degree of modulation of the expression of said genes normally observed for skin of a subject of approximately 25 years of age.

6. The method of claim 1, wherein at least five different genes are selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN.

7. A method according to claim 1 or claim 2, wherein said measuring or said comparing is carried out within 72 hours following the physical challenge.

8. A method according to claim 1 or claim 2, further comprising determining if the differential analysis of the expression of at least one of the genes selected from the group consisting of ESRRA, CBX3, MAP3K5, TRIO, PIK3CD, TCRB, PRRG2, ICP22BP, GPX3, GBA, BPGM, NID1, SMT3H2, LGALS2, DOC1 and PRKCG differs by more than 50% from the mean modulation normally observed for skin of a subject approximately 25 years of age.

9. A method of measuring mRNA transcription in skin that has been treated with a treatment comprising the steps of
   i) performing the method of claim 1 on a human subject before treating the skin of the human subject with a treatment;
   ii) treating the skin of the human subject with the treatment;
   ii) performing the method of claim 1 on the human subject after treating the skin of the human subject with the treatment.

10. A method of measuring mRNA transcription in skin that has been treated with a molecule comprising the steps of
   i) performing the method of claim 1 on a human subject before treating the skin of the human subject with a molecule;
   ii) treating the skin of the human subject with the molecule;

ii) performing the method of claim 1 on the human subject after treating the skin of the human subject with the molecule.

11. The method of claim 10 further comprising determining if at least one of the following conditions is observed:
an acceleration in the modulation kinetics of at least one of genes KRTB6 and KRT16;
an inhibition of induction after 30 hours of at least one gene selected from the group consisting of ESRRA, CBX3, MAP3K5, TRIO, PIK3CD, TCRB, PRRG2, ICP22BP, GPX3, GBA, BPGM, NID1, SMT3H2, LGALS2, DOC1, and PRKCG; and,
a modification of the intensity of modulation of at least one gene selected from the group consisting of S100A8, S100A9, S100A2, S100A7, K15, SPRR1B and GSN, wherein said modification is a difference from mean modulation normally observed in skin of a subject approximately 25 years of age.

12. The method of claim 9, further comprising
normalizing the modulation of the mRNA transcription of the selected genes with respect to the mRNA transcription of at least one gene selected from the group consisting of S100A10, EIF1, ACTR1A, RPL28, RPL5, RPL35, RPS13, RPS23, RPS16, RPL18, RPS15A, RPL7A, RPS28, G3BP1, TMSB4X, HLA-C, DYNLL1, NACA, ARHA, BAI2, UBA52 and GNAS in the epidermis corresponding to the region challenged by tape-stripping.

13. The method of claim 9, wherein at least five different genes are selected from the group consisting of KRT6B, KRT16, ESRRA, CBX3, MAP3K5, TRIO, PIK3CD, TCRB, PRRG2, ICP22BP, GPX3, GBA, BPGM, NID1, SMT3H2, LGALS2, DOC1, PRKCG, S100A8, S100A9, S100A2, S100A7, K15, SPRR1B and GSN.

14. The method according to claim 9, wherein said second sample is removed after 30 hours following tape-stripping.

* * * * *